United States Patent
Meyer et al.

(10) Patent No.: US 9,427,557 B2
(45) Date of Patent: *Aug. 30, 2016

(54) OCCLUSION CROSSING DEVICE AND METHOD

(75) Inventors: Michael Meyer, Richfield, MN (US); Michael Wayne Davis, Rockford, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 482 days.

This patent is subject to a terminal disclaimer.

(21) Appl. No.: 13/352,739

(22) Filed: Jan. 18, 2012

(65) Prior Publication Data

US 2012/0116491 A1    May 10, 2012

Related U.S. Application Data

(63) Continuation of application No. 12/178,425, filed on Jul. 23, 2008, now Pat. No. 8,109,985.

(51) Int. Cl.
*A61F 2/06* (2013.01)
*A61M 25/10* (2013.01)
(Continued)

(52) U.S. Cl.
CPC .... *A61M 25/1002* (2013.01); *A61B 17/12136* (2013.01); *A61B 17/12172* (2013.01);
(Continued)

(58) Field of Classification Search
CPC .............. A61B 17/12136; A61B 2017/12127; A61B 17/12172; A61B 2017/22067; A61B 2017/22068; A61B 2017/22069; A61B 2017/3435; A61B 1/00151; A61F 2/95; A61F 2002/9528; A61F 2002/9534; A61F 2/966; A61F 2/958; A61M 25/1002; A61M 2025/1004; A61M 2025/1015; A61M 2025/1065; A61M 2025/1068; A61M 2025/109; A61M 2025/1052; A61M 25/0116; A61M 25/0119
USPC ........... 623/1.11; 604/96.01, 101.01, 101.03, 604/101.04, 101.05, 103, 103.03, 604/103.06–103.07, 104–106
See application file for complete search history.

(56) References Cited

U.S. PATENT DOCUMENTS 3,769,981 A * 11/1973 McWhorter ............. 604/102.03
4,243,040 A * 1/1981 Beecher .......... A61B 17/22032
                                                         604/271
(Continued)

FOREIGN PATENT DOCUMENTS

WO    97/24154    7/1997
WO    01/70325    9/2001
(Continued)

OTHER PUBLICATIONS

Chan, Albert W. et al., "Rotaglide-Facilitated Stent Delivery: Mission Accomplished," Catheterization and Cardiovascular Interventions, vol. 59 (2003) pp. 477-481.
(Continued)

*Primary Examiner* — David C Eastwood
*Assistant Examiner* — Erin Colello
(74) *Attorney, Agent, or Firm* — Seager, Tufte & Wickhem LLP

(57) ABSTRACT

A stent delivery catheter for positioning a stent across a lesion of a blood vessel is disclosed. The catheter includes an inflation balloon coupled to a distal region of the elongate shaft of the catheter and a stent loaded on the inflation balloon. The catheter may also include an occlusion balloon having a proximal waist secured to the elongate shaft and a distal waist secured to the elongate shaft. The occlusion balloon includes a first folded-over portion extending distal of the distal waist to a distalmost extent of the occlusion balloon and a second folded-over portion extending proximal of the proximal waist to a proximalmost extent of the occlusion balloon. The catheter further includes a fluid discharge port located distal of the occlusion balloon for discharging a lubricious fluid exterior of the elongate shaft toward the stent to facilitate advancing the stent across an occlusion.

18 Claims, 20 Drawing Sheets

(51) Int. Cl.
*A61B 17/12* (2006.01)
*A61F 2/958* (2013.01)
*A61B 17/22* (2006.01)
*A61F 2/90* (2013.01)
*A61M 25/00* (2006.01)

(52) U.S. Cl.
CPC ...... *A61F2/958* (2013.01); *A61B 2017/22067* (2013.01); *A61F 2/90* (2013.01); *A61M 25/0021* (2013.01); *A61M 25/0068* (2013.01); *A61M 2025/1004* (2013.01); *A61M 2025/1015* (2013.01); *A61M 2025/1052* (2013.01)

(56) References Cited

U.S. PATENT DOCUMENTS

| | | | |
|---|---|---|---|
| 4,469,100 A | 9/1984 | Hardwick | |
| 4,655,746 A * | 4/1987 | Daniels et al. | 604/509 |
| 4,921,478 A | 5/1990 | Solano et al. | |
| 5,163,906 A | 11/1992 | Ahmadi | |
| 5,279,546 A | 1/1994 | Mische et al. | |
| 5,439,446 A | 8/1995 | Barry | |
| 5,462,529 A * | 10/1995 | Simpson et al. | 604/101.04 |
| 5,484,412 A | 1/1996 | Pierpont | |
| 5,591,129 A * | 1/1997 | Shoup et al. | 604/103.1 |
| 5,728,068 A | 3/1998 | Leone et al. | |
| 5,833,650 A | 11/1998 | Imran | |
| 5,919,163 A | 7/1999 | Glickman | |
| 6,022,340 A | 2/2000 | Sepetka et al. | |
| 6,039,721 A * | 3/2000 | Johnson | A61F 2/958 604/103 |
| 6,090,097 A * | 7/2000 | Barbut et al. | 604/511 |
| 6,146,373 A * | 11/2000 | Cragg et al. | 604/523 |
| 6,156,005 A | 12/2000 | Theron | |
| 6,206,868 B1 | 3/2001 | Parodi | |
| 6,210,408 B1 | 4/2001 | Chandrasekaran et al. | |
| 6,221,042 B1 | 4/2001 | Adams | |
| 6,290,689 B1 * | 9/2001 | Delaney et al. | 604/507 |
| 6,391,832 B2 | 5/2002 | Lyons et al. | |
| 6,413,235 B1 | 7/2002 | Parodi | |
| 6,461,294 B1 | 10/2002 | Oneda et al. | |
| 6,485,500 B1 * | 11/2002 | Kokish et al. | 606/194 |
| 6,533,753 B1 | 3/2003 | Haarstad et al. | |
| 6,595,953 B1 * | 7/2003 | Coppi et al. | 604/96.01 |
| 6,620,148 B1 | 9/2003 | Tsugita | |
| 6,679,879 B2 * | 1/2004 | Shadduck | 606/41 |
| 6,706,013 B1 * | 3/2004 | Bhat et al. | 604/96.01 |
| 6,730,063 B2 * | 5/2004 | Delaney et al. | 604/173 |
| 6,730,117 B1 | 5/2004 | Tseng et al. | |
| 6,776,793 B2 | 8/2004 | Brown et al. | |
| 6,929,633 B2 | 8/2005 | Evans et al. | |
| 6,945,993 B2 | 9/2005 | Kveen et al. | |
| 6,960,222 B2 | 11/2005 | Vo et al. | |
| 6,966,902 B2 * | 11/2005 | Tsugita et al. | 604/509 |
| 6,981,986 B1 | 1/2006 | Brown et al. | |
| 7,090,655 B2 | 8/2006 | Barry | |
| 7,166,120 B2 | 1/2007 | Kusleika | |
| 7,824,370 B2 | 11/2010 | Hirszowicz et al. | |
| 7,860,556 B2 * | 12/2010 | Saadat | 600/476 |
| 7,887,560 B2 | 2/2011 | Kusleika | |
| 8,172,792 B2 * | 5/2012 | Wang et al. | 604/101.03 |
| 8,343,170 B2 * | 1/2013 | Massicotte et al. | 606/127 |
| 2001/0011182 A1 * | 8/2001 | Dubrul et al. | 606/200 |
| 2002/0022859 A1 | 2/2002 | Hogendijk | |
| 2002/0095147 A1 * | 7/2002 | Shadduck | 606/41 |
| 2002/0165574 A1 | 11/2002 | Ressemann et al. | |
| 2002/0188253 A1 * | 12/2002 | Gordon et al. | 604/101.03 |
| 2003/0023204 A1 | 1/2003 | Vo et al. | |
| 2003/0105508 A1 * | 6/2003 | Johnson | A61F 2/958 623/1.11 |
| 2003/0208223 A1 * | 11/2003 | Kleiner | 606/198 |
| 2004/0093061 A1 * | 5/2004 | Acosta et al. | 623/1.11 |
| 2005/0256565 A1 | 11/2005 | Barry | |
| 2006/0229701 A1 | 10/2006 | Gurm et al. | |
| 2007/0038178 A1 * | 2/2007 | Kusleika | 604/103.03 |
| 2007/0038227 A1 * | 2/2007 | Massicotte | A61B 17/22032 606/127 |
| 2007/0088380 A1 * | 4/2007 | Hirszowicz et al. | 606/194 |
| 2007/0150044 A1 * | 6/2007 | Wang | A61F 2/958 623/1.11 |

FOREIGN PATENT DOCUMENTS

| | | | |
|---|---|---|---|
| WO | 02/051490 | 7/2002 | |
| WO | 2005/102184 | 11/2005 | |
| WO | WO 2005102184 A1 * | 11/2005 | A61B 17/22 |
| WO | 2006/130326 | 12/2006 | |

OTHER PUBLICATIONS

Dobies, David R. et al., "Case Reports: Injecting Lubricant Into the Guiding Catheter Enables Stent Deployment," HMP Communications, (2007) 1 sheet.

Kanehira, E., et al., "How Secure are the Arteries Occluded by a Newly Developed Ultrasonically Activated Device?" Surgical Endoscopy, vol. 13 (1999) pp. 340-342.

Singh, Alok, M.D. et al., "Facilitated Stent Delivery Using Applied Topical Lubrication," Catheterization and Cardiovascular Interventions, vol. 69 (2007) pp. 218-222.

Voeltz, Michele D., M.D. et al., "The Important Properties of Contrast Media: Focus on Viscosity," The Journal of Invasive Cardiology, vol. 19, Supplement A (Mar. 2007) pp. 1A-9A.

* cited by examiner

OCCLUSION CROSSING DEVICE AND METHOD

RELATED APPLICATIONS

This application is a continuation of U.S. application Ser. No. 12/178,425, filed Jul. 13, 2008, the entire disclosure of which is incorporated herein by reference.

TECHNICAL FIELD

The disclosure is directed to elongated medical devices. More particularly, the disclosure is directed to balloon catheters and stent delivery devices for positioning a balloon and/or stent across a lesion of a blood vessel.

BACKGROUND

Millions of people suffer from thrombotic or atherosclerotic occlusions in blood vessels. Such occlusions restrict the blood flow through the vessel, and if left untreated, these occlusions may lead to a heart attack, or even death. A variety of available medical devices have been manufactured to treat occlusions in a blood vessel within a patient's body. For example, directional atherectomy and percutaneous translumenal coronary angioplasty (PTCA) with or without stent deployment have been found useful in treating patients with coronary occlusions, as well as occlusions of other vessels. Angioplasty utilizes an expandable balloon on a catheter which exerts a mechanical force on the vascular wall to enlarge the luminal diameter of an occluded vessel. In some medical procedures, a prosthetic device, such as a stent, is expanded within the blood vessel at the location of the occlusion in order to provide patency/integrity through the lumen of the blood vessel at the location of the occlusion.

Some vascular occlusions can be difficult or impossible to cross with existing angioplasty catheters and stent delivery systems. For example, in some instances the occlusion may extend substantially across the lumen of the blood vessel, or may even completely block the lumen of the blood vessel in some cases. In such instances, it may be difficult or impossible to advance a conventional catheter, such as the balloon of a conventional angioplasty catheter (i.e., POBA) and/or a stent of a stent delivery system, across the occlusion.

Therefore, a need remains to provide a catheter system to aid in crossing vascular occlusions with a balloon and/or a stent of a balloon catheter. Namely, it would be desirable to provide a means for facilitating advancement of a balloon, stent and/or other working element of a catheter through the restricted opening of a vascular occlusion of a blood vessel.

SUMMARY

The disclosure is directed to several alternative designs, materials and methods of manufacturing medical device structures and assemblies.

Accordingly, one illustrative embodiment is a stent delivery catheter for positioning a stent across a lesion of a blood vessel. The catheter includes an inflation balloon coupled to a distal region of the elongate shaft of the catheter and a stent loaded on the inflation balloon. The inflation balloon includes a proximal waist, a distal waist and a central region between the proximal waist and the distal waist. The catheter may also include an occlusion balloon having a proximal waist secured to the elongate shaft and a distal waist secured to the elongate shaft. The occlusion balloon includes a first folded-over portion extending distal of the distal waist to a distalmost extent of the occlusion balloon and a second folded-over portion extending proximal of the proximal waist to a proximalmost extent of the occlusion balloon. The catheter further includes a fluid discharge port located distal of the occlusion balloon for discharging a fluid exterior of the elongate shaft. The fluid may be a lubricious fluid discharged toward the stent to facilitate advancing the stent across an occlusion.

Another illustrative embodiment is a stent delivery catheter for positioning a stent across a lesion of a blood vessel. The catheter includes an inflation balloon coupled to a distal region of the elongate shaft of the catheter and a stent loaded on the inflation balloon. The inflation balloon includes a proximal waist, a distal waist and a central region between the proximal waist and the distal waist. The catheter may also include an occlusion balloon having a proximal waist secured to the elongate shaft and a distal waist secured to the elongate shaft. The occlusion balloon includes a first portion extending distal of the distal waist to a distalmost extent of the occlusion balloon which is not bonded to the elongate shaft, and a second portion extending proximal of the proximal waist to a proximalmost extent of the occlusion balloon which is not bonded to the elongate shaft. The catheter further includes a fluid discharge port located distal of the occlusion balloon for discharging a fluid exterior of the elongate shaft.

Another illustrative embodiment is a stent delivery catheter for positioning a stent across a lesion of a blood vessel. The catheter includes an inflation balloon coupled to a distal region of the elongate shaft of the catheter and a stent loaded on the inflation balloon. The inflation balloon includes a proximal waist, a distal waist and a central region between the proximal waist and the distal waist. The catheter may also include an occlusion member configured to expand across a lumen of a blood vessel. The occlusion member is disposed around the elongate shaft at a location proximal of the inflation balloon. The elongate shaft is longitudinally translatable relative to the occlusion member. The catheter further includes a fluid discharge port located distal of the occlusion balloon for discharging a fluid exterior of the elongate shaft.

Another illustrative embodiment is a method of crossing a lesion within a blood vessel with a stent delivery catheter. The method includes providing a stent delivery catheter including an elongate shaft, an inflation balloon, a stent disposed over the inflation balloon, an occlusion balloon, and a fluid discharge port. A guidewire is advanced through a lumen of a blood vessel and across a lesion within the blood vessel. The stent delivery catheter is then advanced over the guidewire such that the inflation balloon and stent are located just proximal of the lesion. The occlusion balloon is then inflated such that the occlusion balloon extends across the lumen of the blood vessel. A lubricious fluid is expelled out the fluid discharge port into the blood vessel. The inflation balloon and stent may then be further advanced across the lesion while retaining the occlusion balloon at least partially inflated. With the stent across the lesion, the inflation balloon may be inflated, thereby expanding the stent within the lumen of the blood vessel at the lesion. Prior to withdrawing the catheter from the blood vessel, the inflation balloon and the occlusion balloon may be at least partially deflated.

Yet another illustrative embodiment is a method of crossing a lesion within a blood vessel with a stent delivery catheter. The method includes providing a stent delivery catheter including an elongate shaft, an inflation balloon, a stent disposed over the inflation balloon, an occlusion device, and a fluid discharge port. A guidewire is advanced through a lumen of a blood vessel and across a lesion within the blood vessel. The stent delivery catheter is then advanced over the guidewire such that the inflation balloon and stent are located just proximal of the lesion. The occlusion device is then expanded such that the occlusion device extends across the lumen of the blood vessel. A lubricious fluid is expelled out the fluid discharge port into the blood vessel. The inflation balloon and stent may then be further advanced across the lesion while retaining the occlusion device at least partially expanded within the blood vessel. With the stent across the lesion, the inflation balloon may be inflated, thereby expanding the stent within the lumen of the blood vessel at the lesion. Prior to withdrawing the catheter from the blood vessel, the inflation balloon may be at least partially deflated and the occlusion device may be at least partially collapsed.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
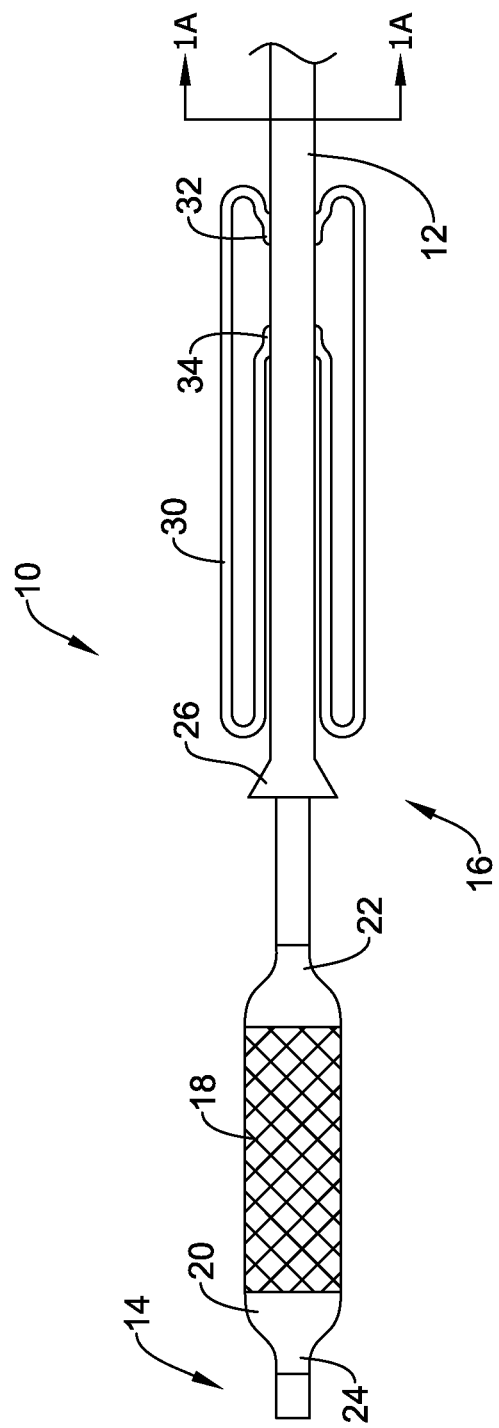
FIG. 1 is a plan view of an exemplary stent delivery catheter for crossing an occlusion within a blood vessel.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Now referring to FIG. 1, an exemplary medical device, shown as a stent delivery catheter system 10, is illustrated. The stent delivery catheter 10 includes an elongate shaft 12 extending from a proximal end (not shown) to a distal end 14. The elongate shaft 12 includes a distal region 16 proximate the distal end 14 of the elongate shaft 12. An inflation balloon 20 may be secured to the elongate shaft 12 along the distal region 16 of the elongate shaft 12. For instance, a proximal waist 22 of the inflation balloon 20 may be secured to the elongate shaft 12 and/or a distal waist 24 of the inflation balloon 20 may be secured to the elongate shaft 12. In some embodiments, the proximal waist 22 and/or the distal waist 24 of the inflation balloon 20 may be bonded, such as adhesively bonded or thermally bonded, to the elongate shaft 12.

In some embodiments, the elongate shaft 12 may be a multi-lumen elongate member, such as an extruded multi-lumen elongate member. In other embodiments, the elongate shaft 12 may include an outer tubular member and an inner tubular member disposed within the lumen of the outer tubular member. In such an embodiment, the proximal waist 22 of the inflation balloon 20 may be secured to the outer tubular member and the distal waist 24 of the inflation balloon 20 may be secured to the inner tubular member.

A stent 18, or other prosthetic device, may be loaded onto the inflation balloon 20. For instance, the stent 18 may be disposed on and extend around the circumference of a central region of the inflation balloon 20. Although illustrated as a stent 18, any number of devices that may be introduced subcutaneously, percutaneously or surgically may be loaded onto the inflation balloon 20. The stent 18 may be any desired stent. Some exemplary stents are disclosed in U.S. Pat. Nos. 6,730,117; 6,776,793; 6,945,993 and 6,981,986, each of which are incorporated herein by reference. In some embodiments, the stent 18 may have a longitudinal length of about 8 to about 40 millimeters, about 10 to about 20 millimeters, about 12 to about 18 millimeters, or about 14 to about 16 millimeters.

The stent delivery catheter 10 may include a fluid discharge port 26 at a location in the distal region 16 of the elongate shaft 12. For example, the fluid discharge port 26 may be located proximal of the inflation balloon 20. However, in other embodiments, the fluid discharge port 26 may be located distal of the inflation balloon 20.

The fluid discharge port 26 may be configured to discharge a fluid, such as a lubricious fluid or a therapeutic agent, out of the elongate shaft 12 and into the lumen of a blood vessel during delivery of the stent 18 to a target location of a patient's body. In some embodiments, the fluid discharge port 26 may be configured such that a fluid expelled from the fluid discharge port 26 is directed toward the stent 18, toward the distal end 14 of the stent delivery catheter 10, and/or toward an occlusion blocking advancement of the stent delivery catheter 10 further distally through a blood vessel.

An occlusion member, shown as an occlusion balloon 30, may be located proximal of the fluid discharge port 26. For example, the occlusion balloon 30 may be secured to the elongate shaft 12 at a location proximal of the inflation balloon 20 and the fluid discharge port 26. In some embodiments, the fluid discharge port 26 may be located intermediate the inflation balloon 20 and the occlusion balloon 30. The occlusion balloon 30 may include a proximal waist 32 secured to the elongate shaft 12 and/or a distal waist 34 secured to the elongate shaft 12. In some embodiments, the proximal waist 32 and/or the distal waist 34 of the occlusion balloon 30 may be bonded, such as adhesively bonded or thermally bonded, to the elongate shaft 12.

Figure 1A:
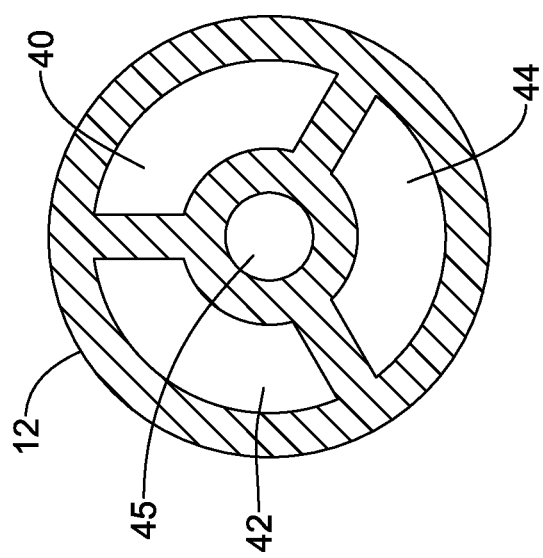
FIG. 1A is a cross-sectional view of the elongate shaft of FIG. 1 taken along line 1A-1A proximal of the occlusion balloon.

FIG. 1A is a cross-sectional view of the elongate shaft 12 at a location proximal of the occlusion balloon 30 taken along line 1A-1A of FIG. 1. The elongate shaft 12 may include a plurality of lumens. For example, the elongate shaft 12 may include a guidewire lumen 45 for receiving a guidewire. The guidewire lumen 45 may extend from the distal end 14 of the elongate shaft 12 to a location proximal of the inflation balloon 20 and/or the occlusion balloon 30. In some instances, the guidewire lumen 45 may extend from the distal end 14 of the elongate shaft 12 to the proximal end of the elongate shaft 12, while in other instances, the guidewire lumen 45 may extend proximally from the distal end 14 of the elongate shaft 12 to a guidewire exit port located distal of the proximal end of the elongate shaft 12.

Additionally, the elongate shaft 12 may include a first inflation lumen 40 in fluid communication with the interior of the inflation balloon 20 for advancing an inflation fluid distally through the elongate shaft 12 to the inflation balloon 20. The elongate shaft 12 may also include a second inflation lumen 42 in fluid communication with the interior of the occlusion balloon 30 for advancing an inflation fluid distally through the elongate shaft 12 to the occlusion balloon 30. Thus, it can be seen that the inflation balloon 20 and the occlusion balloon 30 may each be inflated/deflated independently of inflation/deflation of the other of the inflation balloon 20 and the occlusion balloon 30.

The elongate shaft 12 may further include a fluid injection lumen 44 in fluid communication with the fluid discharge port 26. During use, a fluid, such as a lubricious fluid or a therapeutic agent, may be injected from exterior of the body of a patient through the elongate shaft 12 via the fluid injection lumen 44 to the fluid discharge port 26. Thus, a fluid, such as a lubricious fluid or a therapeutic agent, may be expelled from the fluid discharge port 26 into a blood vessel of a patient while the stent delivery catheter 10 is located within a blood vessel of a patient.

Although the elongate shaft 12 is shown including a guidewire lumen 45 centrally located between three additional lumens, one of skill in the art would understand that the elongate shaft 12 may include any desired number and arrangement of lumens to accomplish a desired function.

Figure 2:
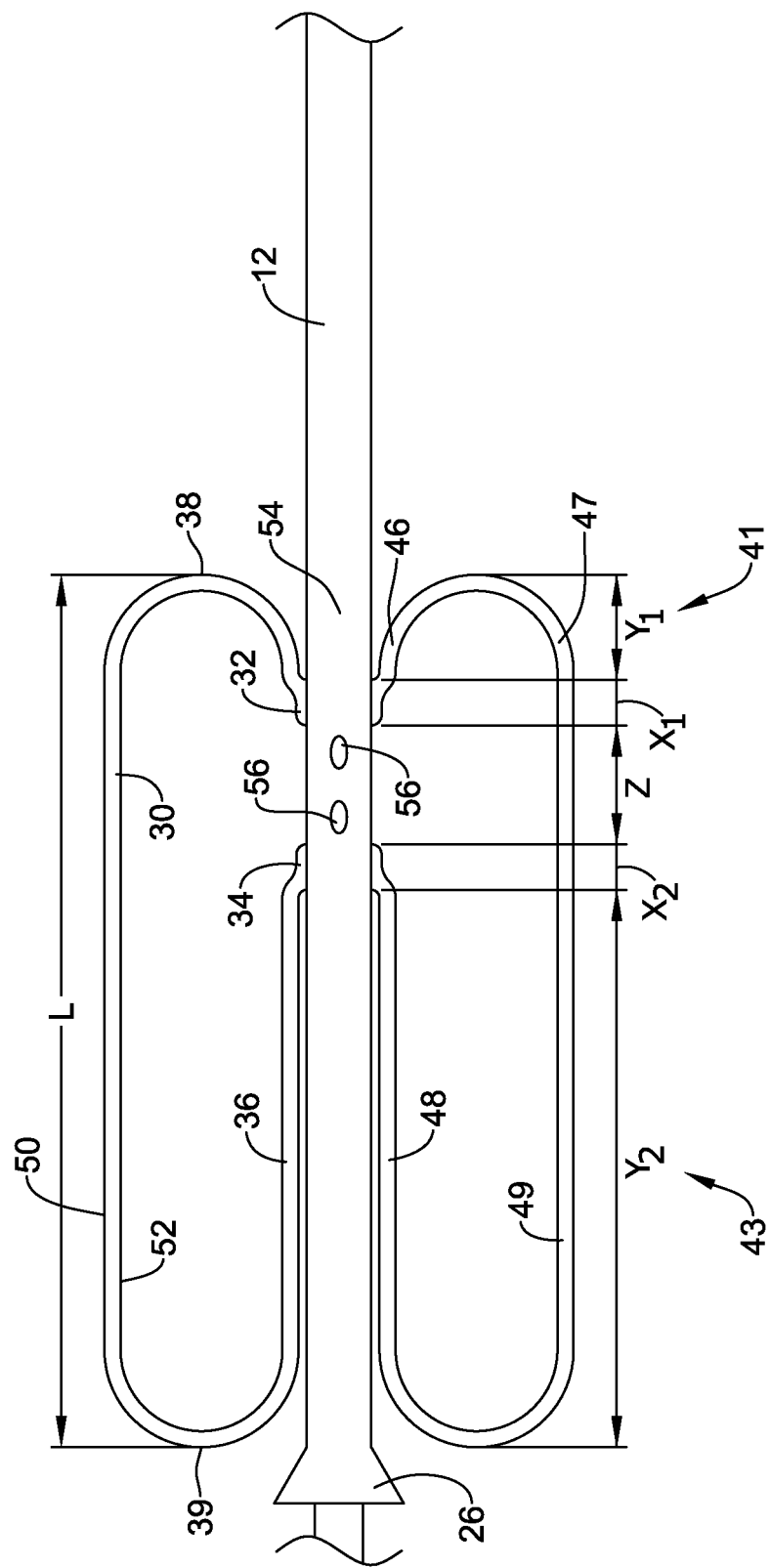
FIGS. 2 through 4 are partial cross-sectional views of a distal portion of the stent delivery catheter depicting rolling movement of the occlusion balloon.

Now referring to FIG. 2, the occlusion balloon 30 will be further described. The occlusion balloon 30 is shown in its expanded or inflated state in FIG. 2. The occlusion balloon 30 may be formed of a balloon wall 36 extending between the proximal waist 32 and the distal waist 34 of the occlusion balloon 30. The occlusion balloon 30 may have a longitudinal length L measured from a proximalmost extent 38 of the occlusion balloon 30 to a distalmost extent 39 of the occlusion balloon 30.

In some embodiments, the occlusion balloon 30 may be formed of a non-compliant material, such as a non-compliant polymeric material. Thus, when inflated, the occlusion balloon 30 will not continue to enlarge in size and/or shape beyond a predetermined expanded size and shape as the fluid pressure within the occlusion balloon 30 continues to increase. In other embodiments, the occlusion balloon 30 may be formed of a compliant material, such as an elastomeric polymer. In some embodiments, the diameter of the occlusion balloon 30 may be sized smaller than the diameter of the inflation balloon 20. For example, in some embodiments, the diameter of the occlusion balloon 30 when inflated may be chosen to be about 10%, about 15%, about 20%, about 25% or about 30% less than the diameter of the inflation balloon 20 when inflated.

As shown in FIG. 2, the proximal waist 32 and the distal waist 34 of the occlusion balloon 30 may be secured to the elongate shaft 12 at locations underneath the occlusion balloon 30. The distance between the proximal waist 32 and the distal waist 34 is denoted as length Z in FIG. 2. Furthermore, the longitudinal length of the proximal waist 32 (e.g., the portion of the occlusion balloon 30 bonded to the elongate shaft 12) is denoted as length $X_1$, and the longitudinal length of the distal waist 34 (e.g., the portion of the occlusion balloon 30 bonded to the elongate shaft 12) is denoted as length $X_2$.

In some embodiments, the length Z between the proximal waist 32 and the distal waist 34 may be less than the length L of the occlusion balloon 30. For instance, in some embodiments the length L of the occlusion balloon 30 may be about 1.5 times or more, about 2 times or more, about 2.5 times or more, about 3 times or more, about 3.5 times or more, about 4 times or more, about 4.5 times or more, or about 5 times or more of the length Z between the proximal waist 32 and the distal waist 34 of the occlusion balloon 30.

The occlusion balloon 30 may include a first folded-over (i.e., doubled-over) portion 41 located proximal of the proximal waist 32 and a second folded-over (i.e., doubled-over) portion 43 located distal of the distal waist 34. The first folded-over portion 41 includes a first layer 46 of the occlusion balloon wall 36 and a second layer 47 of the occlusion balloon wall 36 located radially outward from the first layer 46 of the occlusion balloon wall 36. The second folded-over portion 43 includes a first layer 48 of the occlusion balloon wall 36 and a second layer 49 of the occlusion balloon wall 36 located radially outward from the first layer 48 of the occlusion balloon wall 36.

The first layer 46 of the first folded-over portion 41 may extend proximal of the proximal balloon waist 32 to the proximalmost extent 38 of the occlusion balloon 30, and the first layer 48 of the second folded-over portion 43 may extend distal of the distal balloon waist 34 to the distalmost extent 39 of the occlusion balloon 30.

The second layer 47 of the first folded-over portion 41 may extend distally from the proximalmost extent 38 of the occlusion balloon 30 at a position radially outward from the first layer 46, and the second layer 49 of the second folded-over portion 43 may extend proximally from the distalmost extent 39 of the occlusion balloon 30 at a position radially outward from the first layer 48.

The first layer 46 of the first folded-over portion 41 may extend circumferentially around the circumference of the elongate shaft 12, and the second layer 47 of the first folded-over portion 41 may extend circumferentially around the circumference of the elongate shaft 12 radially outward of the first layer 46. Furthermore, the first layer 48 of the second folded-over portion 43 may extend circumferentially around the circumference of the elongate shaft 12, and the second layer 49 of the second folded-over portion 43 may extend circumferentially around the circumference of the elongate shaft 12 radially outward of the first layer 48.

The wall 36 of the occlusion balloon 30 has an exterior surface 50 and an interior surface 52. As described herein, the exterior surface 50 is the surface of the wall 36 of the occlusion balloon 30 which may come into contact with blood within a blood vessel and/or the inner surface (e.g., intima) of a blood vessel during use. As described herein, the interior surface 52 is the surface of the wall 36 of the occlusion balloon 30 which may come into contact with an inflation fluid used to inflate the occlusion balloon 30 during use. The exterior surface 50 of the first layer 46 of the first folded-over portion 41 may face the exterior surface 54 of the elongate shaft 12. However, the exterior surface 50 of the first layer 46 may not be secured to the exterior surface 54 of the elongate shaft 12. Thus, the first layer 46 of the first folded-over portion 41 may extend along the exterior surface 54 of the elongate shaft 12, yet not be bonded to the elongate shaft 12. Likewise, the exterior surface 50 of the first layer 48 of the second folded-over portion 43 may face the exterior surface 54 of the elongate shaft 12. However, the exterior surface 50 of the first layer 48 may not be secured to the exterior surface 54 of the elongate shaft 12. Thus, the first layer 48 of the second folded-over portion 43 may extend along the exterior surface 54 of the elongate shaft 12, yet not be bonded to the elongate shaft 12.

The longitudinal length of the first folded-over portion 41 proximate the proximalmost extent 38 of the occlusion balloon 30 is denoted as $Y_1$ in FIG. 2 and the longitudinal length of the second folded over portion 43 proximate the distalmost extent 39 of the occlusion balloon 30 is denoted as $Y_2$ in FIG. 2. In some embodiments, the sum of the longitudinal lengths of the first folded-over portion 41 and the second folded-over portion 43 is equal to or greater than the length of the stent 18. For instance, in some embodiments the sum of the longitudinal lengths of the first folded-over portion 41 and the second folded-over portion 43 may be about 1 or more times, about 1.1 or more times, 1.2 or more times, 1.3 or more times, 1.4 or more times, 1.5 or more times, 2 or more times, or 2.5 or more times the length of the stent 18.

Figure 3:
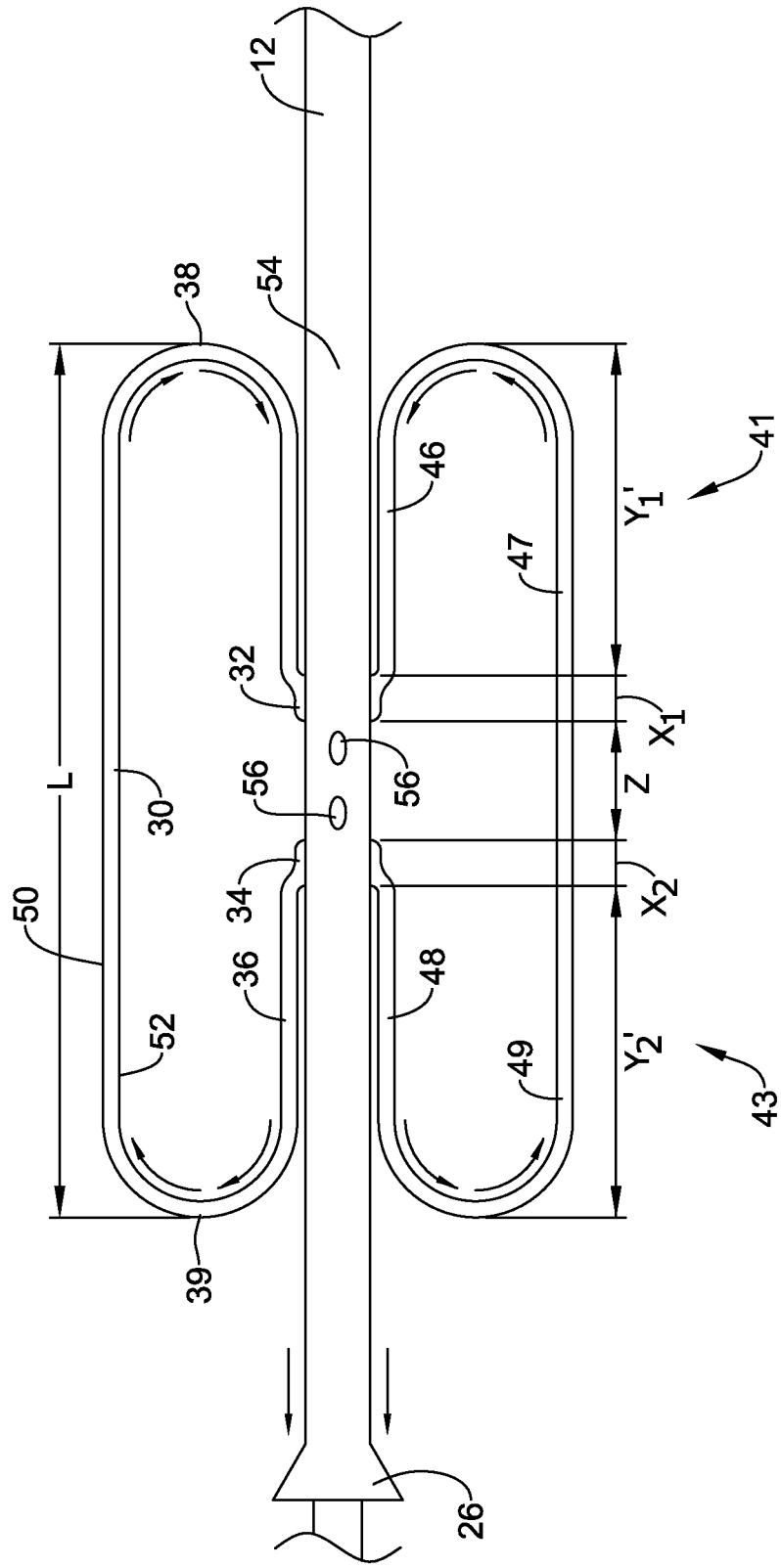

The configuration of the occlusion balloon 30 allows the occlusion balloon 30 to roll upon itself while the occlusion balloon 30 is at least partially inflated within a blood vessel. This is demonstrated in FIG. 3. As shown in FIG. 3, distal advancement of the elongate shaft 12 while the occlusion balloon 30 is at least partially inflated and in contact with the intima of a blood vessel causes the occlusion balloon 30 to roll upon itself. In other words, as the elongate shaft 12 is advanced distally (shown by arrows in FIG. 3), a portion of the first layer 48 of the second folded-over portion 43 of the occlusion balloon 30 rolls away from the exterior surface 54 of the elongate shaft 12 and becomes a portion of the second layer 49 of the second folded-over portion 43 of the elongate shaft 12. Similarly, a portion of the second layer 47 of the first folded-over portion 41 of the occlusion balloon 30 rolls toward the exterior surface 54 of the elongate shaft 12 and becomes a portion of the first layer 46 of the first folded over portion 41. This movement of the balloon wall 36 is depicted by the arrows interior of the occlusion balloon 30 shown in FIG. 3.

Such rolling motion increases the length of the first folded-over portion 41 from the length $Y_1$ shown in FIG. 2 to the length $Y_1'$ shown in FIG. 3. Similarly, such rolling motion reduces the length of the second folded-over portion 43 from the length $Y_2$ shown in FIG. 2 to the length $Y_2'$ shown in FIG. 3. Although the length $Y_1'$ of the first folded-over portion 41 and the length $Y_2'$ of the second folded-over portion 43 of the occlusion balloon 30 are changed, it is noted that the sum of the length $Y_1'$ of the first folded-over portion 41 and the length $Y_2'$ of the second folded-over portion 43 may remain the same, as the occlusion balloon 30 undergoes rolling action. Additionally, the overall longitudinal length L of the occlusion balloon 30 may remain unchanged throughout the rolling motion. Furthermore, as the occlusion balloon 30 is rolled upon itself as the elongate shaft 12 is advanced distally, the distance between the distal extent 39 of the occlusion balloon 30 and the fluid discharge port 26 increases.

Figure 4:
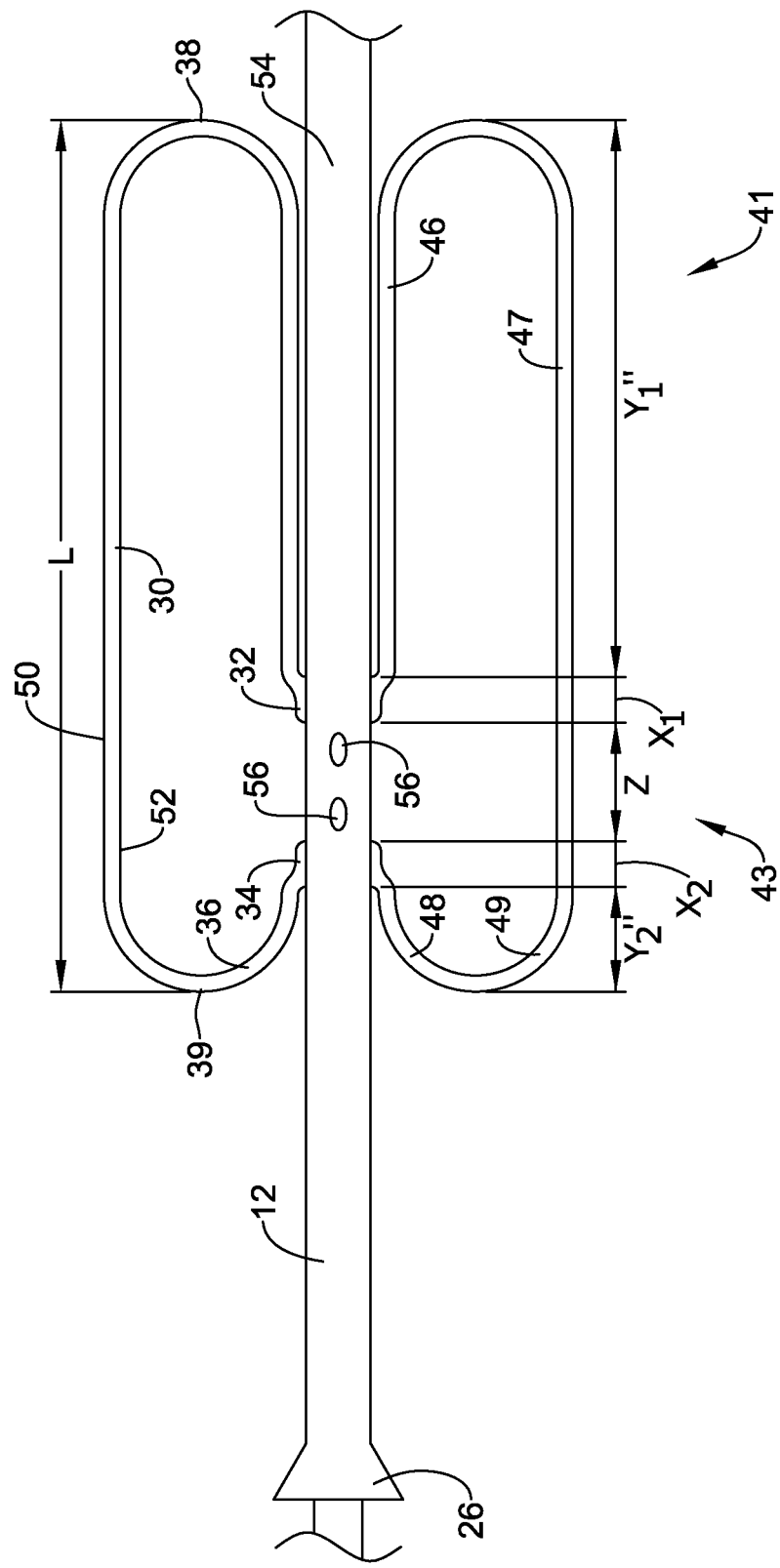

FIG. 4 shows the elongate shaft 12 advanced further distally relative to the occlusion balloon 30. As shown in FIG. 4, further distal advancement of the elongate shaft 12 while the occlusion balloon 30 is at least partially inflated and in contact with the intima of a blood vessel causes the occlusion balloon 30 to further roll upon itself. In other words, as the elongate shaft 12 is further advanced distally (from the position shown in FIG. 3), an additional portion of the first layer 48 of the second folded-over portion 43 of the occlusion balloon 30 rolls away from the exterior surface 54 of the elongate shaft 12 and becomes a portion of the second layer 49 of the second folded-over portion 43 of the elongate shaft 12. Similarly, an additional portion of the second layer 47 of the first folded-over portion 41 of the occlusion balloon 30 rolls toward the exterior surface 54 of the elongate shaft 12 and becomes a portion of the first layer 46 of the first folded over portion 41.

Such rolling motion further increases the length of the first folded-over portion 41 from the length $Y_1'$ shown in FIG. 3 to the length $Y_1''$ shown in FIG. 4. Similarly, such rolling motion further reduces the length of the second folded-over portion 43 from the length $Y_2'$ shown in FIG. 3 to the length $Y_2''$ shown in FIG. 4. Although the length $Y_1''$ of the first folded-over portion 41 and the length $Y_2''$ of the second folded-over portion 43 of the occlusion balloon 30 are changed, it is noted that the sum of the length $Y_1''$ of the first folded-over portion 41 and the length $Y_2''$ of the second folded-over portion 43 may remain the same, as the occlusion balloon 30 undergoes further rolling action. As the occlusion balloon 30 is further rolled upon itself as the elongate shaft 12 is advanced distally, the distance between the distal extent 39 of the occlusion balloon 30 and the fluid discharge port 26 further increases.

The elongate shaft 12 may include one or more, or a plurality of inflation ports 56 fluidly connecting the second inflation lumen 42 of the elongate shaft 12 with the interior of the occlusion balloon 30. The inflation port(s) 56 allow an inflation fluid to enter the interior of the occlusion balloon 30 during inflation of the occlusion balloon 30 from the second inflation lumen 42.

Figure 5:
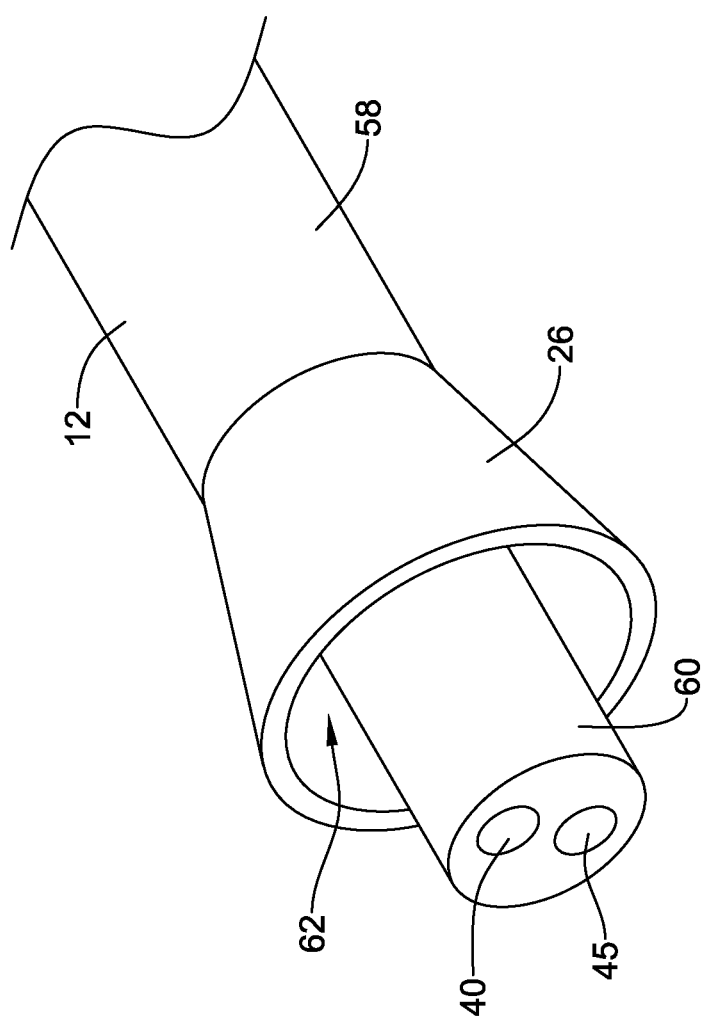
FIG. 5 is a perspective view of a portion of the catheter of FIG. 1 showing the fluid discharge port.

FIG. 5 is a perspective view further illustrating one possible configuration of the fluid discharge port 26. As shown in FIG. 5, the elongate shaft 12 may include a proximal section 58 and a distal section 60 extending distal of the proximal section 58. The distal section 60 may include the guidewire lumen 45 and the first inflation lumen 40 which is in fluid communication with the interior of the inflation balloon 20 of the stent delivery catheter 10. In other embodiments, such as embodiments in which the fluid discharge port 26 is located distal of the inflation balloon 20, the distal section 60 of the elongate shaft 12 may include one or more additional lumens.

The fluid discharge port 26 may be located at the distal end of the proximal section 58. For example, in some embodiments the fluid discharge port 26 may be a conical or funnel-shaped portion of the proximal section 58 concentrically disposed around the distal section 60 extending distally from the proximal section 58. The opening 62 of the fluid discharge port 26 may be in fluid communication with the fluid injection lumen 44 of the elongate shaft 12. The conical nature of the fluid discharge port 26 may allow a fluid, such as a lubricious fluid or a therapeutic agent, to be expelled from the fluid discharge port 26 substantially around the entire circumference of the distal section 60. Thus, in such an embodiment fluid discharged from the fluid discharge port 26 may be expelled radially outward from the shaft 12 in all radial directions.

FIGS. 6A through 6G illustrate one exemplary method of using the stent delivery catheter 10 during a medical procedure. For example, the stent delivery catheter 10 may be used to place a stent 18 across an occlusion 102, such as a thrombotic or atherosclerotic occlusion, in a blood vessel 100.

Figure 6A:
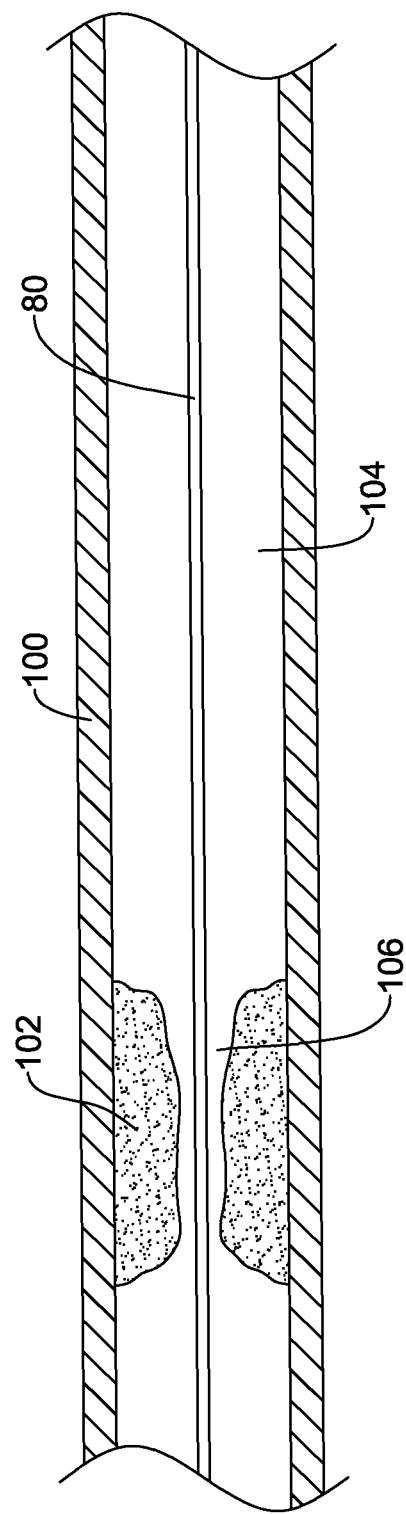
FIGS. 6A through 6G illustrate an exemplary method of placing a stent across an occlusion in a blood vessel utilizing the stent delivery catheter of FIG. 1.

As shown in FIG. 6A, a guidewire 80 may first be advanced through the lumen 104 of the blood vessel 100 such that the guidewire 80 is positioned across the occlusion 102. In some embodiments the guidewire 80 may be passed through an opening 106 extending through the occlusion 102. In other embodiments, the guidewire 80, or another medical device, may form an opening 106 through the occlusion 102. The guidewire 80 may provide a pathway for advancing additional medical devices through the blood vessel 100 to a location proximate the occlusion 102.

Figure 6B:
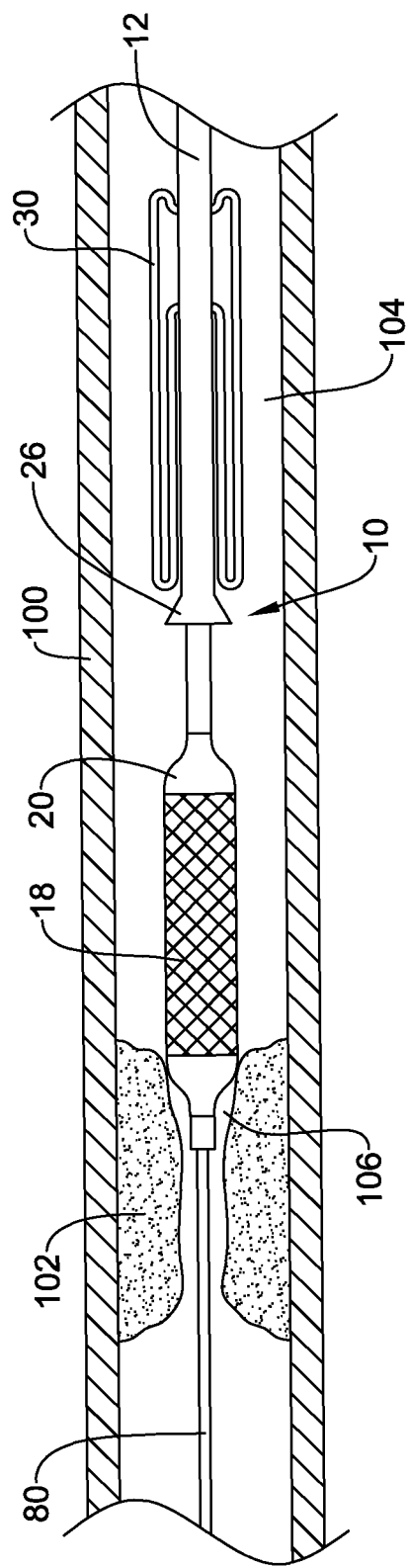

The stent delivery catheter 10 may then be advanced along the guidewire 80 to a location proximate the occlusion 102, as shown in FIG. 6B. For instance, the guidewire 80 may be inserted through the guidewire lumen 45 of the stent delivery catheter 10, and the stent delivery catheter 10 advanced distally thereon. In the case of an occlusion 102 substantially obstructing the lumen 104 of the blood vessel 100, the stent 18 positioned on the stent delivery catheter 10 may not be able to be advanced through the opening 106 and across the occlusion 102 without aid. As shown in FIG. 6B, the presence of the occlusion 102 across the lumen 104 of the blood vessel 100 may halt distal advancement of the stent delivery catheter 10 while the stent 18 of the stent delivery catheter remains proximal of the occlusion 102. In other words, the opening 106 through the occlusion 102 may be too small to allow the stent 18 to pass through the opening 106 unimpeded.

Figure 6C:
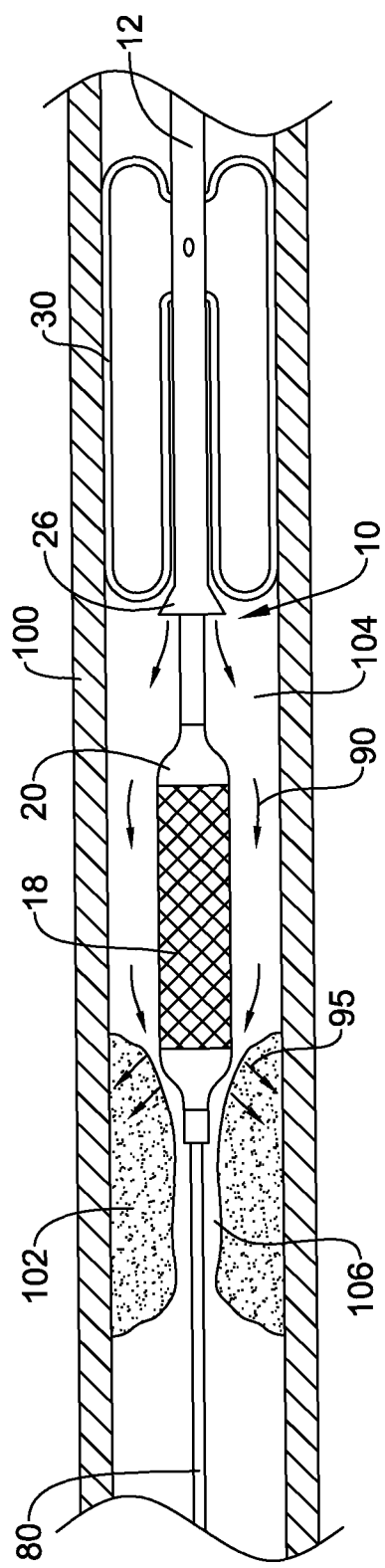

In applications in which the occlusion 102 blocks free advancement of the stent 18 across the occlusion 102, once the stent 18, loaded on the inflation balloon 20 of the stent delivery catheter 10, is located proximal of the occlusion 102, the occlusion balloon 30 may be inflated within the blood vessel 100, as shown in FIG. 6C. Inflation of the occlusion balloon 30 causes the exterior surface 50 of the wall 36 of the occlusion balloon 30 to contact the intima (i.e., inner surface) of the blood vessel 100. Thus when inflated, the occlusion balloon 30 may extend across the lumen 104 of the blood vessel 100. In some embodiments, the occlusion balloon 30 may be inflated to about 2 to about 6 Atmospheres (ATM), or about 2 to about 4 ATM, for example.

In some embodiments, inflation of the occlusion balloon 30 may also help center the elongate shaft 12 and/or the stent 18 of the stent delivery catheter 10 within the lumen 104 of the blood vessel 100. For instance, inflation of the occlusion balloon 30 may align the stent 18 at the center of the lumen 104 of the blood vessel 100.

Inflation of the occlusion balloon 30 within the lumen 104 of the blood vessel 100 may substantially occlude the lumen 104 of the blood vessel 100, preventing blood flow across the location in which the occlusion balloon 30 is inflated. For example, in embodiments in which the occlusion balloon 30 is placed in the upstream direction of blood flow past the occlusion 102, the occlusion balloon 30 may disrupt blood flow across the occlusion balloon 30 toward the occlusion 102.

Once the occlusion balloon 30 is inflated within the blood vessel 100, a fluid, such as a lubricious fluid or a therapeutic agent, (shown by arrows 90) may be expelled from the fluid discharge port 26 into the lumen 104 of the blood vessel 100. The presence of the occlusion balloon 30 may help direct the fluid toward the stent 18 and/or toward the occlusion 102. Furthermore, in some embodiments, such as embodiments in which the occlusion balloon 30 is placed in the upstream direction of blood flow past the occlusion 102, expansion of the occlusion balloon 30 helps prevent the blood flow from disrupting discharge of the fluid 90 from the fluid discharge port 26 into the blood vessel 26 proximate the occlusion 102.

One exemplary lubricious fluid which may be expelled from the fluid discharge port 26 is ROTAGLIDE®, a phospholipid emulsion, sold by Boston Scientific Scimed, Inc., Maple Grove, Minn. ROTAGLIDE® is a solution of olive oil, egg yolk phospholipids, glycerin, sodium deoxycholate, L-histidine, disodium EDTA, sodium hydroxide, and water. In some embodiments, other phospholipid emulsions, oil-in-water based emulsions, as well as other lubricious fluids may be used.

The lubricious fluid 90 may coat the surface of the stent 18 and/or the inflation balloon 20, and/or may coat the surface of the opening 106 of the occlusion 102. In some embodiments, the lubricious fluid 90 may form a lubricious layer or buffer between the stent 18 and the surface of the opening 106 of the occlusion 102. Therefore, the expulsion of the lubricious fluid 90 may greatly reduce the coefficient of friction between the stent 18 and the surface of the opening 106 through the occlusion 102. For example, the lubricious fluid 90 may reduce the coefficient of friction at the interface between the stent 18 and the surface of the opening 106 of the occlusion 102 to about 0.14 or less, about 0.12 or less, about 0.10 or less, about 0.08 or less, about 0.06 or less, or about 0.04 or less in some embodiments.

In some embodiments, the lubricious fluid 90 expelled from the fluid discharge port 26 may act to expand the opening 106 of the occlusion 102, as well. For instance, as shown by arrows 95 of FIGS. 6C and 6D, the forces of the lubricious fluid 90 may act on the surface of the opening 106 of the occlusion 102 to radially enlarge the opening 106 through the occlusion 102. Enlarging the opening 106 and/or reducing the coefficient of friction between the stent 18 and the surface of the opening 106 of the occlusion 102 may facilitate further advancement of the stent 18 and/or inflation balloon 20 through the opening 106 of the occlusion 102.

Figure 6D:
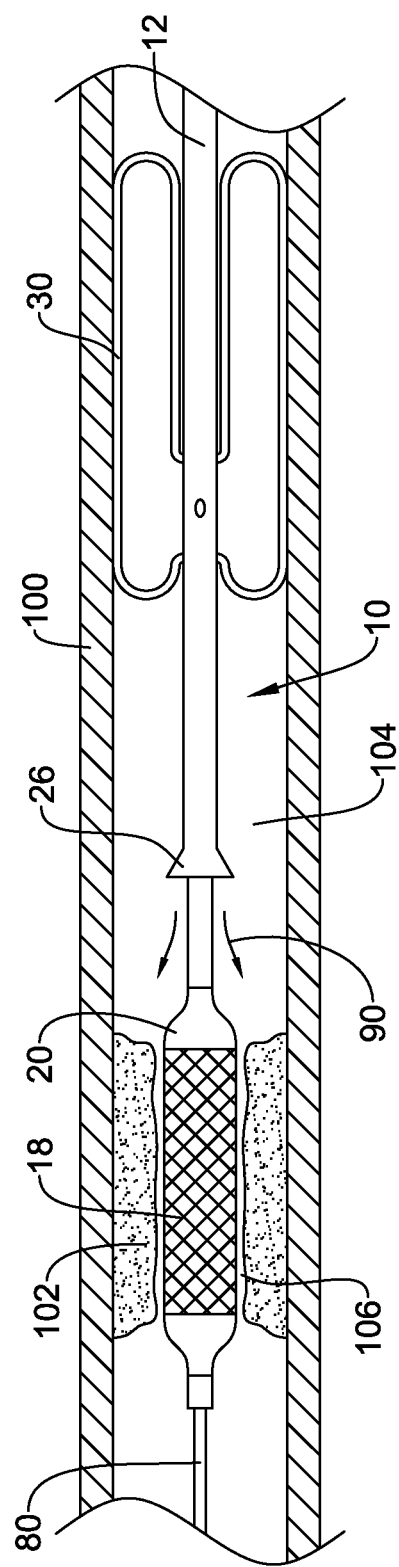

As shown in FIG. 6D, upon expelling the lubricious fluid 90 from the fluid discharge port 26 of the stent delivery catheter 10, the stent 18 and/or the inflation balloon 20 may be further advanced through the opening 106 of the occlusion 102. The stent 18 and/or inflation balloon 20 may be further advanced through the opening 106 of the occlusion 102 while the occlusion balloon 30 remains inflated, or at least partially inflated within the lumen 104 of the blood vessel 100. With the occlusion balloon 30 inflated, or at least partially inflated, the occlusion balloon 30 may remain in contact with the intima or inner surface of the blood vessel 100 while the stent 18 and/or the inflation balloon 20 are further advanced across the occlusion 102.

In some embodiments, while the stent 18 and/or inflation balloon 20 is further advanced through the opening 106 of the occlusion 102, the lubricious fluid 90 may be continuously expelled from the fluid discharge port 26. In other words, in some embodiments the lubricious fluid 90 may be continuously discharged from the fluid discharge port 26 while the stent 18 and/or inflation balloon 20 is further advanced through the opening 106 of the occlusion 102. The lubricious fluid 90 may continue to provide a lubricious barrier between the stent 18 and/or inflation balloon 20 and the inner surface of the opening 106 of the occlusion 102 as the stent 18 and/or inflation balloon 20 is advanced through the opening 106. Additionally and/or alternatively, further discharge of the lubricious fluid 90 may further act on the occlusion 102 to slightly expand the opening 106 of the occlusion 102 as the stent 18 and/or inflation balloon 20 is further advanced through the opening 106.

In other embodiments, while the stent 18 and/or inflation balloon 20 is further advanced through the opening 106 of the occlusion 102, the lubricious fluid 90 may be expelled from the fluid discharge port 26 with periodic pulsations. In other words, in some embodiments the lubricious fluid 90 may be periodically discharged from the fluid discharge port 26 while the stent 18 and/or inflation balloon 20 is further advanced through the opening 106 of the occlusion 102. The pulsations of the lubricious fluid 90 may continue to provide a lubricious barrier between the stent 18 and/or inflation balloon 20 and the inner surface of the opening 106 of the occlusion 102 and/or may further act on the occlusion 102 to slightly expand the opening 106 of the occlusion 102 as the stent 18 and/or inflation balloon 20 is further advanced through the opening 106 and across the occlusion 102.

The configuration of the occlusion balloon 30 allows the elongate shaft 12 and the stent 18 and/or inflation balloon 20 to be advanced further distally within the blood vessel 100 while the occlusion balloon 30 is inflated, or at least partially inflated within the blood vessel 100 to occlude blood flow through the blood vessel 100. As discussed above, further distal movement of the elongate shaft 12 while the occlusion balloon 30 is in contact with the intima or inner surface of the blood vessel 100 results in the occlusion balloon 30 rolling upon itself. This rolling action is illustrated in FIGS. 2-4, which show the proximal waist 32 and the distal waist 34 of the occlusion balloon 30 moving distally while the portion of the wall 36 of the occlusion balloon 30 in contact with the blood vessel 100 does not move longitudinally relative to the blood vessel 100 at the interface between the occlusion balloon 30 and the inner surface of the blood vessel 100.

As can be seen by comparing the position of the occlusion balloon 30 shown in FIG. 6C with the position of the occlusion balloon 30 shown in FIG. 6D, as the elongate shaft 12, inflation balloon 20 and/or stent 18 are further advanced distally through the occlusion 102, a portion of the exterior surface of the occlusion balloon 30 facing the exterior surface of the elongate shaft 12 moves into contact with the intima of the blood vessel 100. Simultaneously, a portion of the exterior surface of the occlusion balloon 30 in contact with the intima of the blood vessel 100 loses contact with the intima of the blood vessel 100 and rolls toward the exterior surface of the elongate shaft 12.

Through the rolling motion of the occlusion balloon 30, the longitudinal length of the folded-over portion of the occlusion balloon 30 extending distally of the distal waist 34 decreases, while the longitudinal length of the folded-over portion of the occlusion balloon 30 extending proximally of the proximal waist 32 increases. The overall length of the occlusion balloon 30 from the distalmost extent of the occlusion balloon 30 to the proximalmost extent of the occlusion balloon 30 may remain the same throughout the rolling motion of the occlusion balloon 30.

The occlusion balloon 30 may be configured such that the elongate shaft 12 of the stent delivery catheter 10 may be advanced distally through a blood vessel 100 at least the length of the stent 18 while the occlusion balloon 30 remains in contact with the inner surface of the blood vessel 100. The rolling action of the occlusion balloon 30 without sliding the occlusion balloon 30 along the inner surface of the blood vessel 100 allows the elongate shaft 12, inflation balloon 20 and/or stent 18 to be advanced distally through the blood vessel 100 while the occlusion balloon 30 is inflated, or at least partially inflated in the blood vessel 100 and in contact with the inner surface of the blood vessel 100 without harming the blood vessel 100.

Figure 6E:
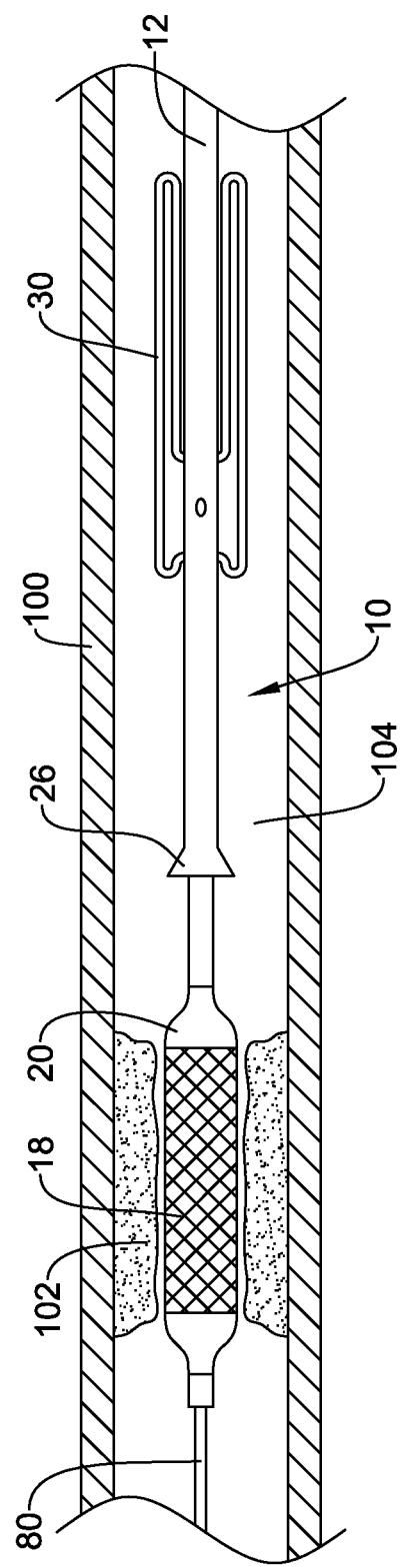
Figure 6F:
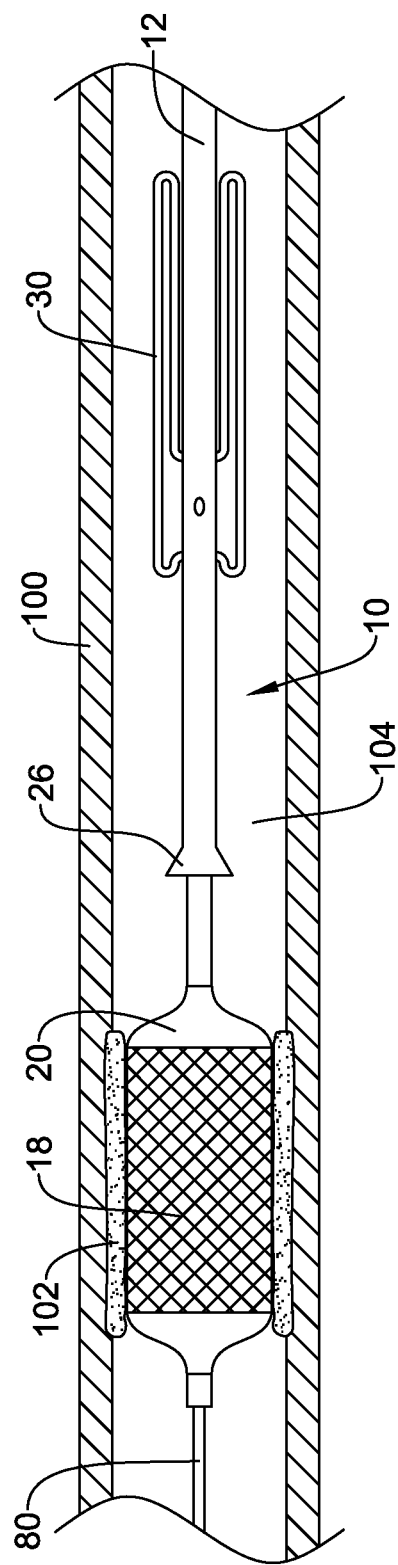

As shown in FIG. 6E, once the stent 18 and/or inflation balloon 20 is positioned through the opening 106 at a desired location, the occlusion balloon 30 may be deflated and/or expulsion of the lubricious fluid 90 from the fluid discharge port 26 may be discontinued. With the stent 18 and/or inflation balloon 20 positioned across the occlusion 102, the inflation balloon 20 may be inflated by injecting a pressurized fluid into the interior of the inflation balloon 20 from the first inflation lumen 40 of the elongate shaft 12. As shown in FIG. 6F, inflation of the inflation balloon 20 causes the opening 106 through the occlusion 102 to expand in order to open the passageway through the occlusion 102 in order to regain blood flow past the occlusion 102. In embodiments in which a stent 18 is placed across the occlusion 102, inflation of the inflation balloon 20 expands the stent 18 into contact with the occlusion 102, opening the occlusion 102 to an enlarged diameter. The expanded stent 18 may help maintain the opening through the occlusion 102, thus contributing to the patency and/or integrity of the blood vessel 100.

Figure 6G:
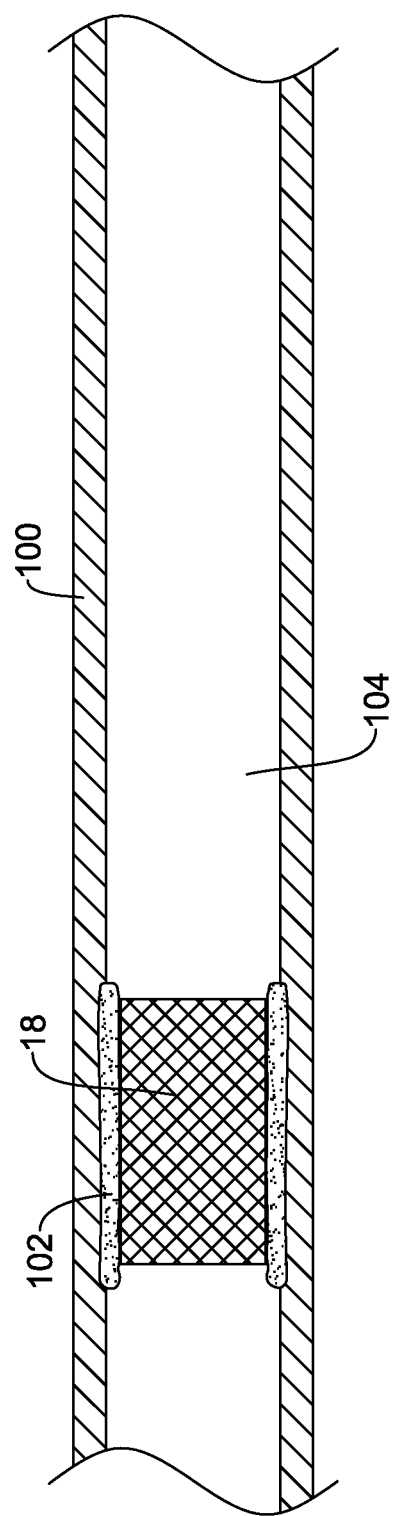

With the stent 18 properly expanded within the blood vessel 100, the inflation balloon 20 may be deflated, or at least partially deflated. The stent delivery catheter 10 may then be withdrawn proximally from the blood vessel 100. Additionally, the guidewire 80 may also be withdrawn from the blood vessel 100 at the conclusion of the medical procedure. As shown in FIG. 6G, at the completion of the medical procedure, the stent 18, if used, may remain expanded across the occlusion 102, enlarging the opening 106 through the occlusion 102, thus improving blood flow through the blood vessel 100.

Although the above method of regaining blood flow across an occlusion 102 in a blood vessel 100 includes implanting a stent 18 across the occlusion 102, in some embodiments the catheter 10 may be used as a conventional angioplasty catheter (e.g., POBA) in which the inflation balloon 20 may be inflated to enlarge the opening through the occlusion 102 without the aid of a stent 18.

Additionally, although the catheter 10 used in the above method of regaining blood flow across an occlusion 102 is discussed as including an occlusion balloon 30, in other embodiments the catheter 10 may not include an occlusion balloon 30. In such embodiments, a lubricious fluid 90 may be expelled from the fluid discharge port 26 toward the stent 18 and/or occlusion 102 without the need of occluding the vessel 100 with an occlusion balloon 30.

Figure 7:
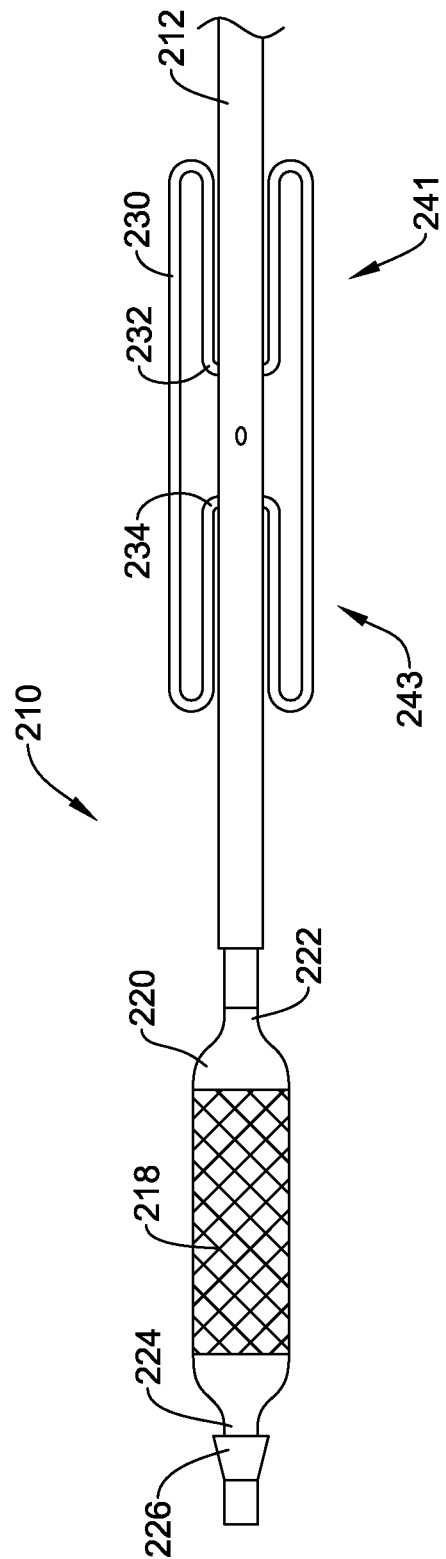
FIG. 7 illustrates the distal portion of another exemplary stent delivery catheter.

FIG. 7 illustrates the distal region of another stent delivery catheter 210. The stent delivery catheter 210 may include an elongate shaft 212 extending from a proximal end of the stent delivery catheter 210 to the distal end of the stent delivery catheter 210. An inflation balloon 220 may be secured to the distal region of the elongate shaft 212. For example, the proximal waist 222 of the inflation balloon 220 may be secured to the elongate shaft 212 and/or the distal waist 224 of the inflation balloon 220 may be secured to the elongate shaft 212. In some embodiments the proximal waist 222 and/or the distal waist 224 may be bonded, such as adhesively or thermally bonded, to the elongate shaft 212.

A stent 218, or other prosthetic device, may be loaded onto the inflation balloon 220. For instance, the stent 218 may be disposed on and extend around the circumference of a central region of the inflation balloon 220. Although illustrated as a stent 218, any number of devices that may be introduced subcutaneously, percutaneously or surgically may be loaded onto the inflation balloon 220.

The stent delivery catheter 210 may also include an occlusion member, such as an occlusion balloon 230, secured to the elongate shaft 212 at a location proximal of the inflation balloon 220. The occlusion balloon 230 may be similar in construction, function and operation to that of the occlusion balloon 30 of the stent delivery catheter 10. Thus, in the interest of brevity, similarities in the construction, function and operation of the occlusion balloon 230 with that of the occlusion balloon 30 will not be reiterated.

For example, the occlusion balloon 230 may include a proximal waist 232 secured to the elongate shaft 212 and a distal waist 234 secured to the elongate shaft 212. The proximal waist 232 may be secured to the elongate shaft 212 at a location distal of the proximalmost extent of the occlusion balloon 230. Additionally, the distal waist 234 may be secured to the elongate shaft 212 at a location proximal of the distalmost extent of the occlusion balloon 230. The occlusion balloon 230 may include a first folded-over portion 241 and a second folded-over portion 243. The first folded-over portion 241 may include a first layer of the occlusion balloon wall and a second layer of the occlusion balloon wall located radially outward from the first layer of the occlusion balloon wall. Similarly, the second folded-over portion 243 may include a first layer of the occlusion balloon wall and a second layer of the occlusion balloon wall located radially outward from the first layer of the occlusion balloon wall.

The occlusion balloon 230 may be configured to roll upon itself as the elongate shaft 212 is advanced through a blood vessel of a patient with the occlusion balloon 230 inflated, or at least partially inflated, and in contact with the inner surface of a blood vessel.

The stent delivery catheter 210 may include a fluid discharge port 226 at a location in the distal region of the elongate shaft 212. For example, the fluid discharge port 226 may be located distal of the inflation balloon 220. However, in other embodiments, the fluid discharge port 226 may be located proximal of the inflation balloon 220.

The fluid discharge port 226 may be configured to discharge a fluid, such as a lubricious fluid, out of the elongate shaft 212 and into the lumen of a blood vessel during delivery of the stent 218 to a target location of a patient's body. In some embodiments the fluid discharge port 226 may be configured such that a fluid expelled from the fluid discharge port 226 is directed toward the stent 218.

Similar to the fluid discharge port 26, the fluid discharge port 226 may be a conical or funnel-shaped component concentrically disposed around the elongate shaft 212. The opening of the fluid discharge port 226 may be in fluid communication with a fluid injection lumen of the elongate shaft 212. The conical nature of the fluid discharge port 226 may allow a fluid, such as a lubricious fluid or a therapeutic agent, to be expelled from the fluid discharge port 226 substantially around the entire circumference of the stent 218. Thus, in such an embodiment fluid discharged from the fluid discharge port 226 may be expelled radially outward from the shaft 212 in all radial directions.

Figure 8:
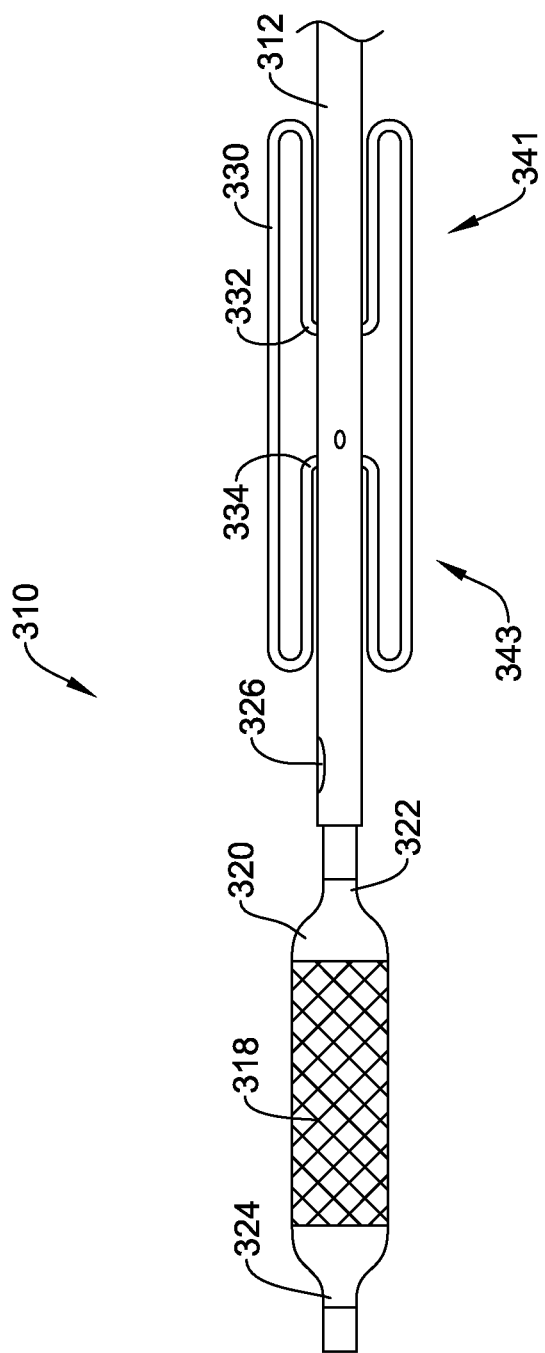
FIG. 8 illustrates the distal portion of another exemplary stent delivery catheter.

FIG. 8 illustrates the distal region of yet another stent delivery catheter 310. The stent delivery catheter 310 may include an elongate shaft 312 extending from a proximal end of the stent delivery catheter 310 to the distal end of the stent delivery catheter 310. An inflation balloon 320 may be secured to the distal region of the elongate shaft 312. For example, the proximal waist 322 of the inflation balloon 320 may be secured to the elongate shaft 312 and/or the distal waist 324 of the inflation balloon 320 may be secured to the elongate shaft 312. In some embodiments, the proximal waist 322 and/or the distal waist 324 may be bonded, such as adhesively or thermally bonded, to the elongate shaft 312.

A stent 318, or other prosthetic device, may be loaded onto the inflation balloon 320. For instance, the stent 318 may be disposed on and extend around the circumference of a central region of the inflation balloon 320. Although illustrated as a stent 318, any number of devices that may be introduced subcutaneously, percutaneously or surgically may be loaded onto the inflation balloon 320.

The stent delivery catheter 310 may also include an occlusion member, such as an occlusion balloon 330, secured to the elongate shaft 312 at a location proximal of the inflation balloon 320. The occlusion balloon 330 may be similar in construction, function and operation to that of the occlusion balloon 30 of the stent delivery catheter 10. Thus, in the interest of brevity, similarities in the construction, function and operation of the occlusion balloon 330 with that of the occlusion balloon 30 will not be reiterated.

For example, the occlusion balloon 330 may include a proximal waist 332 secured to the elongate shaft 312 and a distal waist 334 secured to the elongate shaft 312. The proximal waist 332 may be secured to the elongate shaft 312 at a location distal of the proximalmost extent of the occlusion balloon 330. Additionally, the distal waist 334 may be secured to the elongate shaft 312 at a location proximal of the distalmost extent of the occlusion balloon 330. The occlusion balloon 330 may include a first folded-over portion 341 and a second folded-over portion 343. The first folded-over portion 341 may include a first layer of the occlusion balloon wall and a second layer of the occlusion balloon wall located radially outward from the first layer of the occlusion balloon wall. Similarly, the second folded-over portion 343 may include a first layer of the occlusion balloon wall and a second layer of the occlusion balloon wall located radially outward from the first layer of the occlusion balloon wall.

The occlusion balloon 330 may be configured to roll upon itself as the elongate shaft 312 is advanced through a blood vessel of a patient with the occlusion balloon 330 inflated, or at least partially inflated, and in contact with the inner surface of a blood vessel.

The stent delivery catheter 310 may include a fluid discharge port 326 at a location in the distal region of the elongate shaft 312. For example, the fluid discharge port 326 may be located proximal of the inflation balloon 320. However, in other embodiments, the fluid discharge port 326 may be located distal of the inflation balloon 320.

The fluid discharge port 326 may be configured to discharge a fluid, such as a lubricious fluid or a therapeutic agent, out of the elongate shaft 312 and into the lumen of a blood vessel during delivery of the stent 318 to a target location of a patient's body. In some embodiments, the fluid discharge port 326 may be configured such that a fluid expelled from the fluid discharge port 326 is directed toward the stent 318 and/or inflation balloon 320.

The fluid discharge port 326 may be located at a desired radial location of the elongate shaft 312. For example, the fluid discharge port 326 may be eccentrically located to one side of the elongate shaft 312. The opening of the fluid discharge port 326 may be in fluid communication with a fluid injection lumen of the elongate shaft 312. The location of the fluid discharge port 326 may direct a fluid expelled from the fluid discharge port 326 in a desired radial direction such that fluid discharged from the fluid discharge port 326 is not evenly discharged in all radial directions from the elongate shaft 312. In some embodiments directional discharge of a fluid from the fluid discharge port 326 may be desired. For example, a fluid discharged from the fluid discharge port 326 may be used as a steering mechanism to urge the elongate shaft 312 around a curve and/or away from a wall of a blood vessel.

Figure 9A:
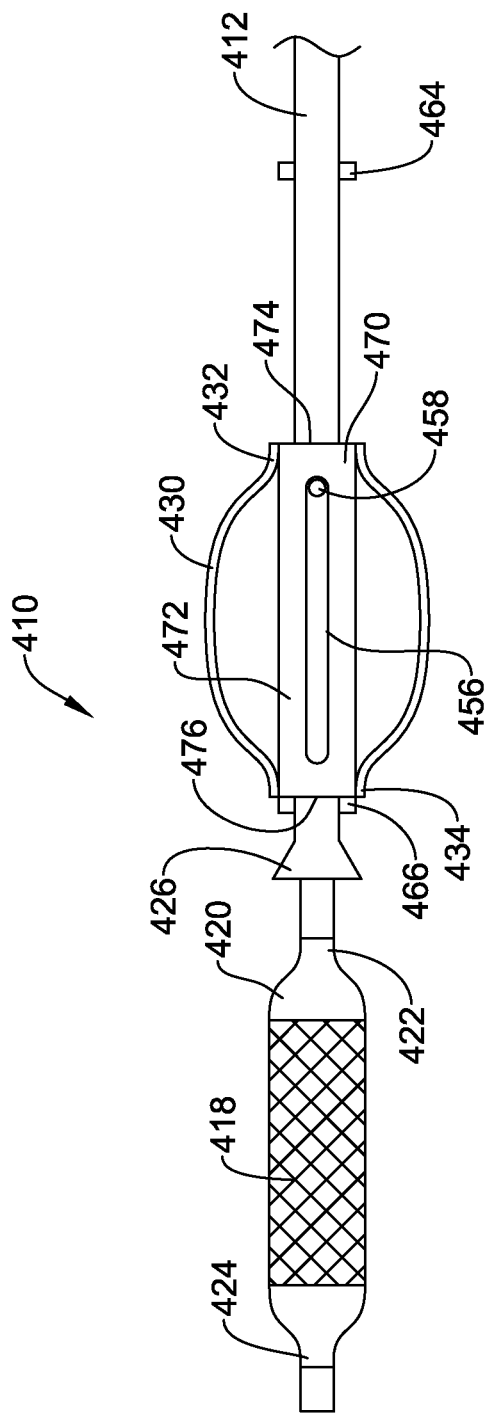
FIGS. 9A and 9B depict another exemplary stent delivery catheter with an elongate shaft translatable through an occlusion member.
Figure 9B:
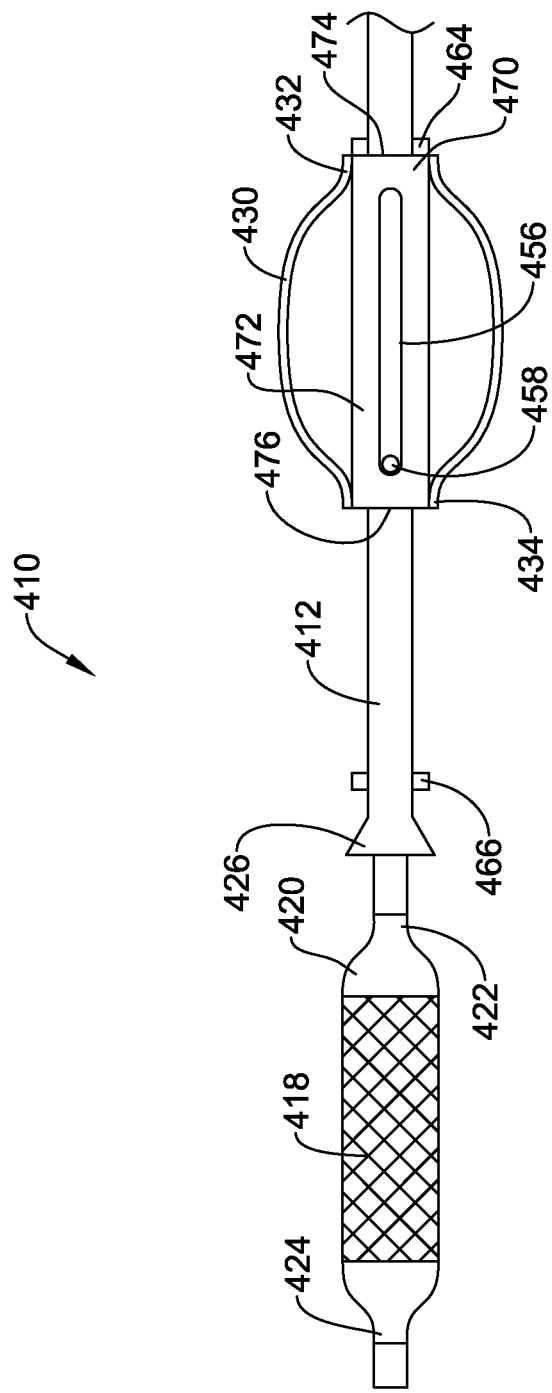

FIGS. 9A and 9B illustrate the distal region of another stent delivery catheter 410. The stent delivery catheter 410 may include an elongate shaft 412 extending from a proximal end of the stent delivery catheter 410 to the distal end of the stent delivery catheter 410. An inflation balloon 420 may be secured to the distal region of the elongate shaft 412. For example, the proximal waist 422 of the inflation balloon 420 may be secured to the elongate shaft 412 and/or the distal waist 424 of the inflation balloon 420 may be secured to the elongate shaft 412. In some embodiments, the proximal waist 422 and/or the distal waist 424 may be bonded, such as adhesively or thermally bonded, to the elongate shaft 412.

A stent 418, or other prosthetic device, may be loaded onto the inflation balloon 420. For instance, the stent 418 may be disposed on and extend around the circumference of a central region of the inflation balloon 420. Although illustrated as a stent 418, any number of devices that may be introduced subcutaneously, percutaneously or surgically may be loaded onto the inflation balloon 420.

The stent delivery catheter 410 may include a fluid discharge port 426 at a location in the distal region of the elongate shaft 412. For example, the fluid discharge port 426 may be located proximal of the inflation balloon 420. However, in other embodiments, the fluid discharge port 426 may be located distal of the inflation balloon 420.

The fluid discharge port 426 may be configured to discharge a fluid, such as a lubricious fluid or a therapeutic agent, out of the elongate shaft 412 and into the lumen of a blood vessel during delivery of the stent 418 to a target location of a patient's body. In some embodiments, the fluid discharge port 426 may be configured such that a fluid expelled from the fluid discharge port 426 is directed toward the stent 418 and/or inflation balloon 420.

Similar to the fluid discharge port 26, the fluid discharge port 426 may be a conical or funnel-shaped component concentrically disposed around the elongate shaft 412. The opening of the fluid discharge port 426 may be in fluid communication with a fluid injection lumen of the elongate shaft 412. The conical nature of the fluid discharge port 426 may allow a fluid, such as a lubricious fluid or a therapeutic agent, to be expelled from the fluid discharge port 426 substantially around the entire circumference of the stent 418 and/or inflation balloon 420. Thus in such an embodiment, fluid discharged from the fluid discharge port 426 may be expelled radially outward from the shaft 412 in all radial directions.

The stent delivery catheter 410 may also include an occlusion member, such as an occlusion balloon 430, disposed about the elongate shaft 412 at a location proximal of the inflation balloon 420 and the fluid discharge port 426. The occlusion member, such as the occlusion balloon 430, may be disposed about the elongate shaft 412 such that the elongate shaft 412 may be longitudinally translatable relative to the occlusion balloon 430. In some embodiments, the occlusion member, such as the occlusion balloon 430, may be longitudinally translatable relative to the elongate shaft 412 a longitudinal length equivalent to or greater than the length of the stent 418. For example, the occlusion balloon 430 may be secured to a sleeve 470 which may be slidably disposed over the elongate shaft 412. The occlusion balloon 430 may include a proximal waist 432 secured to the sleeve 470 and a distal waist 434 secured to the sleeve 470.

As shown in FIGS. 9A and 9B, in some embodiments, the sleeve 470 may be a tubular member 472 having a proximal end 474, a distal end 476, and a lumen extending therethrough. The elongate shaft 412 may be slidably disposed through the lumen of the tubular member 472.

Additionally, the elongate shaft 412 may include a proximal stop 464 proximal of the proximal end 474 of the tubular member 472 and/or a distal stop 466 distal of the distal end 476 of the tubular member 472. The proximal stop 464 may prevent the tubular member 472 from sliding proximal of the proximal stop 464 and the distal stop 466 may prevent the tubular member 472 from sliding distal of the distal stop 466. In other words, the tubular member 472 may be slidably translatable along the elongate shaft 412 between the proximal stop 464 and the distal stop 466.

The tubular member 472 may include a longitudinal slot 456 extending along a length of the tubular member 472. The longitudinal slot 456 may be aligned with an inflation port 458 of the elongate shaft 412. Thus, an inflation fluid may be delivered through an inflation lumen of the elongate shaft 412, through the inflation port 458 and the longitudinal slot 456, and into the interior of the occlusion balloon 430. The longitudinal slot 456 allows the inflation lumen of the elongate shaft 412 to be in fluid communication with the interior of the occlusion balloon 430 regardless of the position of the tubular member 472 between the proximal stop 464 and the distal stop 466. In some embodiments, the stent delivery catheter 410 may also include radial alignment means, such as a groove, tab, or the like, maintaining radial alignment of the inflation port 458 and the longitudinal slot 456 as the elongate shaft 412 is translated through the tubular member 472.

FIG. 9A shows the stent delivery catheter 410 with the elongate shaft 412 fully translated proximally relative to the tubular member 472. As shown in FIG. 9A, the distal end 476 of the tubular member 472 is in contact with the distal stop 466. FIG. 9B shows the stent delivery catheter 410 with the elongate shaft 412 fully translated distally relative to the tubular member 472. As shown in FIG. 9B, the proximal end 474 of the tubular member 472 is in contact with the proximal stop 464.

During use, the stent delivery catheter 410 may be advanced through a blood vessel with the occlusion balloon 430 and the tubular member 472 positioned in their furthest distal position (i.e., with the distal end 476 of the tubular member 472 abutting the distal stop 466). At a desired location within the blood vessel, for example with the stent 418 and/or inflation balloon 420 positioned just proximal of an occlusion, the occlusion balloon 430 may be inflated with an inflation fluid such that the occlusion balloon 430 contacts the inner surface of the blood vessel. While the occlusion balloon 430 is inflated and in contact with the inner surface of a blood vessel, the elongate shaft 412, inflation balloon 420 and/or the stent 418 may be advanced distally through the blood vessel without the occlusion balloon 430 being advanced distally. In other words, the elongate shaft 412 may be translated through the tubular member 472 while the occlusion balloon 430 remains inflated within a blood vessel. In some embodiments, the stent 418 and/or inflation balloon 420 may be advanced distally across an occlusion while the occlusion balloon 430 remains at least partially inflated and expanded across the lumen of the blood vessel.

As the elongate shaft 412 is advanced distally relative to the tubular member 472, the inflation port 458 of the elongate shaft 412 is translated along the longitudinal slot 456 of the tubular member 472. Thus, the interior of the occlusion balloon 430 may remain in fluid communication with the inflation lumen of the elongate shaft 412 throughout the medical procedure.

At the conclusion of the medical procedure, the occlusion balloon 430 may be deflated, or partially deflated prior to removing the stent delivery catheter 410 from the blood vessel. In some embodiments, this may be accomplished by drawing a vacuum through the inflation lumen of the elongate shaft 412 to draw down the occlusion balloon 430.

Figure 10A:
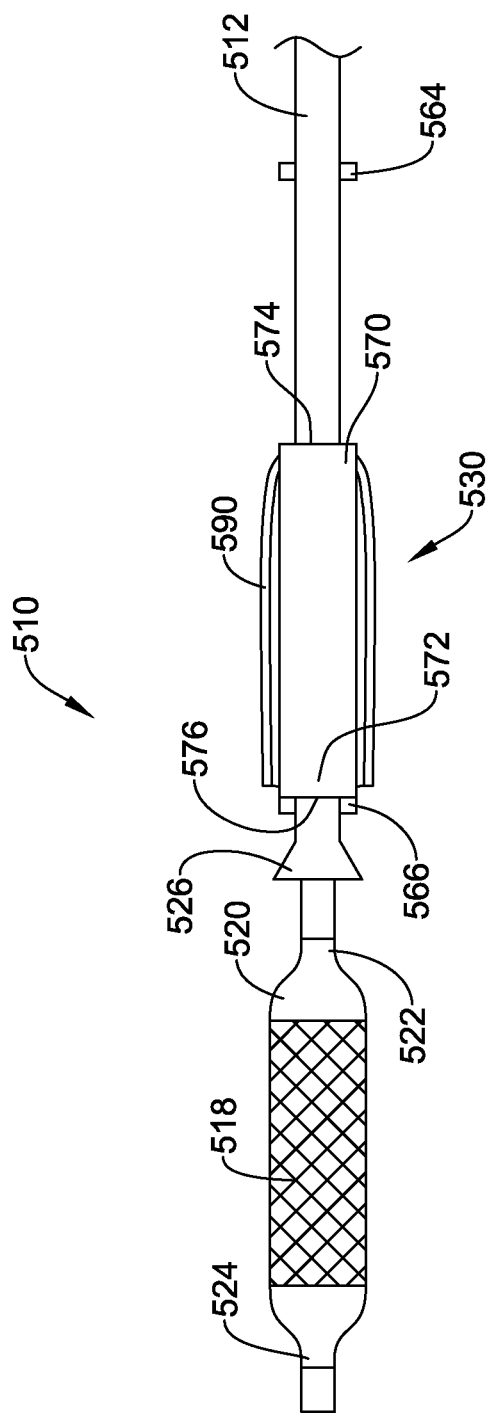
FIGS. 10A through 10C depict another exemplary stent delivery catheter with an elongate shaft translatable through an occlusion member.
Figure 10B:
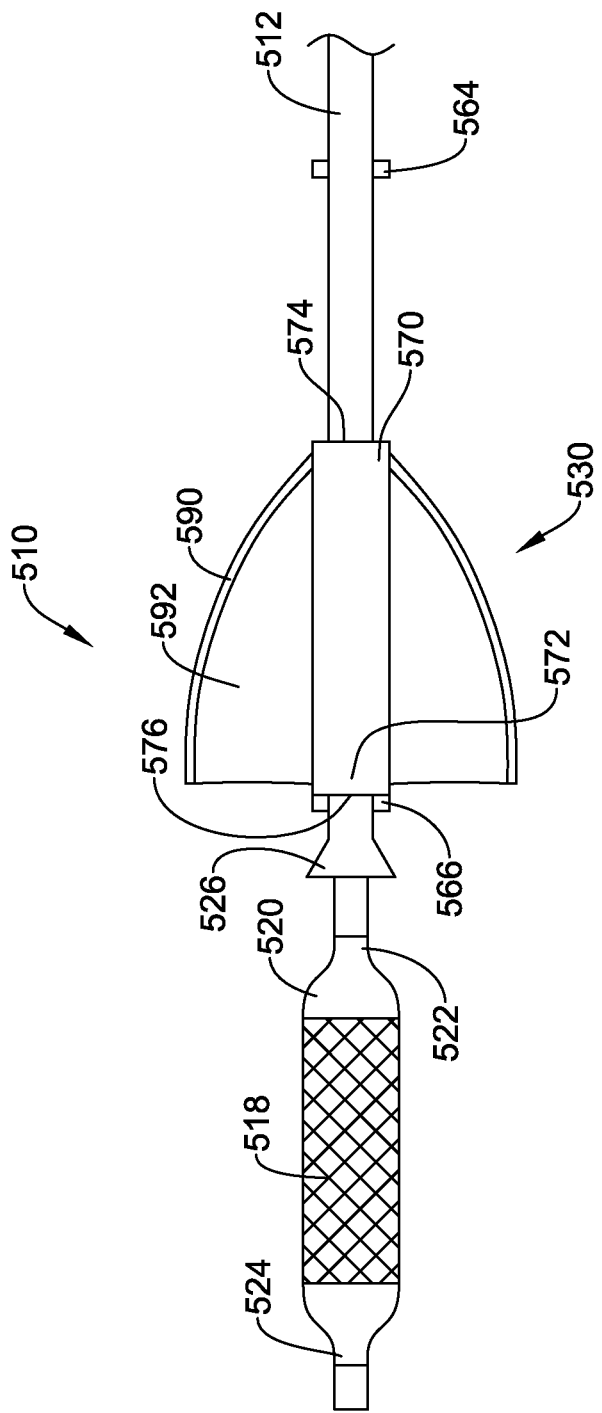
Figure 10C:
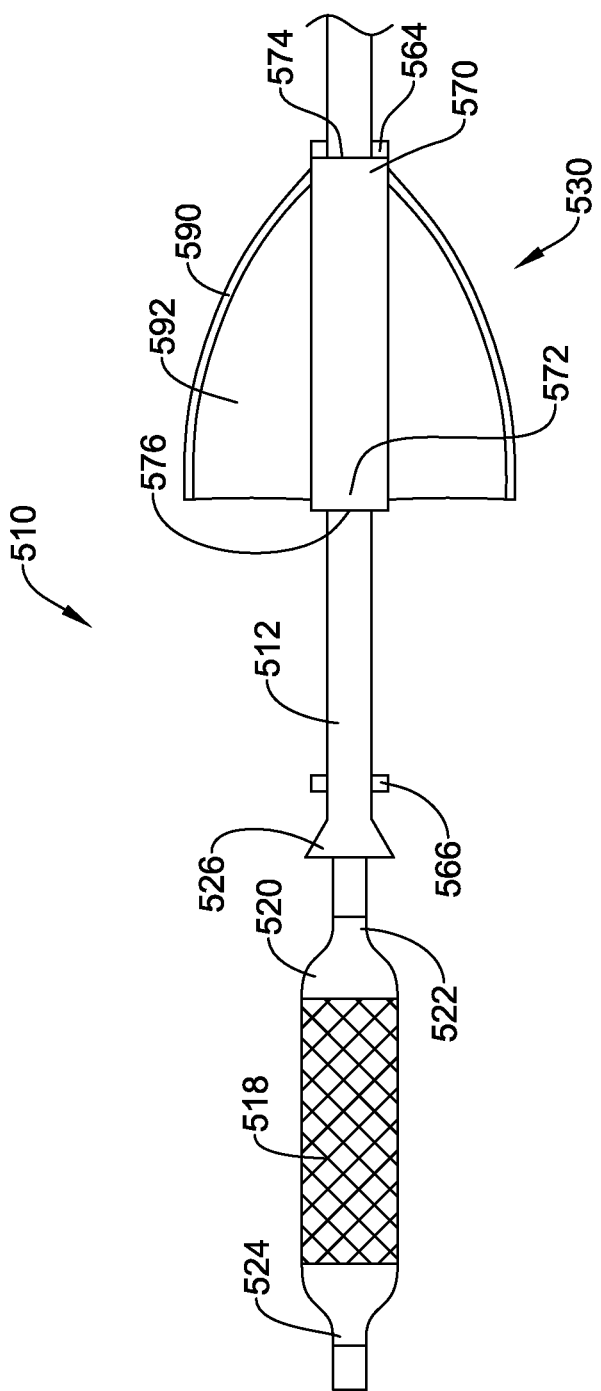

FIGS. 10A through 10C illustrate the distal region of another stent delivery catheter 510. The stent delivery catheter 510 may include an elongate shaft 512 extending from a proximal end of the stent delivery catheter 510 to the distal end of the stent delivery catheter 510. An inflation balloon 520 may be secured to the distal region of the elongate shaft 512. For example, the proximal waist 522 of the inflation balloon 520 may be secured to the elongate shaft 512 and/or the distal waist 524 of the inflation balloon 520 may be secured to the elongate shaft 512. In some embodiments, the proximal waist 522 and/or the distal waist 524 may be bonded, such as adhesively or thermally bonded, to the elongate shaft 512.

A stent 518, or other prosthetic device, may be loaded onto the inflation balloon 520. For instance, the stent 518 may be disposed on and extend around the circumference of a central region of the inflation balloon 520. Although illustrated as a stent 518, any number of devices that may be introduced subcutaneously, percutaneously or surgically may be loaded onto the inflation balloon 520.

The stent delivery catheter 510 may include a fluid discharge port 526 at a location in the distal region of the elongate shaft 512. For example, the fluid discharge port 526 may be located proximal of the inflation balloon 520. However, in other embodiments, the fluid discharge port 526 may be located distal of the inflation balloon 520.

The fluid discharge port 526 may be configured to discharge a fluid, such as a lubricious fluid or a therapeutic agent, out of the elongate shaft 512 and into the lumen of a blood vessel during delivery of the stent 518 to a target location of a patient's body. In some embodiments, the fluid discharge port 526 may be configured such that a fluid expelled from the fluid discharge port 526 is directed toward the stent 518.

Similar to the fluid discharge port 26, the fluid discharge port 526 may be a conical or funnel-shaped component concentrically disposed around the elongate shaft 512. The opening of the fluid discharge port 526 may be in fluid communication with a fluid injection lumen of the elongate shaft 512. The conical nature of the fluid discharge port 526 may allow a fluid, such as a lubricious fluid or a therapeutic agent, to be expelled from the fluid discharge port 526 substantially around the entire circumference of the stent 518. Thus in such an embodiment fluid, discharged from the fluid discharge port 526 may be expelled radially outward from the shaft 512 in all radial directions.

The stent delivery catheter 510 may also include an occlusion member 530 disposed about the elongate shaft 512 at a location proximal of the inflation balloon 520 and the fluid discharge port 526. The occlusion member 530 may be disposed about the elongate shaft 512 such that the elongate shaft 512 may be longitudinally translatable relative to the occlusion member 530. In some embodiments, the occlusion member 530 may be longitudinally translatable relative to the elongate shaft 512 a longitudinal length equivalent to or greater than the length of the stent 518. For example, the occlusion member 530 may include a sleeve 570 which may be slidably disposed over the elongate shaft 512.

As shown in FIGS. 10A through 10C, in some embodiments, the sleeve 570 may be a tubular member 572 having a proximal end 574, a distal end 576, and a lumen extending therethrough. The elongate shaft 512 may be slidably disposed through the lumen of the tubular member 572.

Additionally, the elongate shaft 512 may include a proximal stop 564 proximal of the proximal end 574 of the tubular member 572 and/or a distal stop 566 distal of the distal end 576 of the tubular member 572. The proximal stop 564 may prevent the tubular member 572 from sliding proximal of the proximal stop 564 and the distal stop 566 may prevent the tubular member 572 from sliding distal of the distal stop 566. In other words, the tubular member 572 may be slidably translatable along the elongate shaft 512 between the proximal stop 564 and the distal stop 566.

The occlusion member 530 may include a framework 590, such as an expandable framework, coupled to the tubular member 572. The framework 590 may be movable between a collapsed state, as shown in FIG. 10A, and an expanded state, as shown in FIG. 10B. In the expanded state, the occlusion member 530 may extend substantially across a blood vessel lumen.

A membrane 592 (shown in FIG. 10B), such as a non-permeable membrane, may be attached to the framework 590. Thus, when the framework 590 is expanded radially outward across a blood vessel lumen, the membrane 592 may substantially extend across the blood vessel lumen, inhibiting blood flow past the occlusion member 530. In embodiments utilizing a non-permeable membrane 592, the membrane 592 may generally not allow blood to flow through the membrane 592.

During use, the stent delivery catheter 510 may be advanced through a blood vessel with the occlusion member 530 positioned in its furthest distal position (i.e., with the distal end 576 of the tubular member 572 abutting the distal stop 566). At a desired location within the blood vessel, for example with the stent 518 positioned just proximal of an occlusion, the occlusion member 530 may be expanded such that the occlusion member 530 contacts the inner surface of the blood vessel. For example, the framework 590 of the occlusion member 530 may be radially expanded, moving the non-permeable membrane 592 across the lumen of the blood vessel.

While the occlusion member 530 is expanded and in contact with the inner surface of a blood vessel, the elongate shaft 512, inflation balloon 520 and/or the stent 518 may be advanced distally through the blood vessel without the occlusion member 530 being advanced distally. In other words, as shown in FIG. 10C, the elongate shaft 512 may be translated through the tubular member 572 while the occlusion member 530 remains expanded within a blood vessel. Thus, as the elongate shaft 512 is translated distally through the tubular member 572, the distance between the stent 518 and/or inflation balloon 520 and the occlusion member 530 may increase. In some embodiments, the stent 518 may be advanced distally across an occlusion while the occlusion member 530 remains at least partially expanded across the lumen of the blood vessel.

At the conclusion of the medical procedure, the occlusion member 530 may be retracted, or partially retracted prior to removing the stent delivery catheter 510 from the blood vessel. In some embodiments, this may be accomplished by actuating the framework 590 to draw down the non-permeable membrane 592 of the occlusion member 530. For instance, a retrieval cannula may be advanced over the elongate shaft 512 of the stent delivery catheter 510 to aid in withdrawing the stent delivery catheter from a blood vessel at the conclusion of a medical procedure.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A stent delivery catheter for positioning a stent across a lesion of a blood vessel, the stent delivery catheter comprising:
   an elongate shaft having a proximal end, a proximal region proximate the proximal end, a distal end, and a distal region proximate the distal end;
   an inflation balloon including a proximal waist, a distal waist and a central region between the proximal waist and the distal waist, the inflation balloon secured to the distal region of the elongate shaft;
   a stent having a proximal end, a distal end and a length from the proximal end to the distal end, the stent disposed around the central region of the inflation balloon; and
   an occlusion balloon secured to the elongate shaft proximal of the inflation balloon, the occlusion balloon having a proximal waist secured to the elongate shaft and a distal waist secured to the elongate shaft, the occlusion balloon including a first folded-over portion extending distal of the distal waist to a distalmost extent of the occlusion balloon and a second folded-over portion extending proximal of the proximal waist to a proximalmost extent of the occlusion balloon, the occlusion balloon being inflatable from a pre-inflated state to an inflated state;
   wherein when the occlusion balloon is in the pre-inflated state the first folded-over portion has a length measured from the distal waist of the occlusion balloon to the distalmost extent of the occlusion balloon and the second folded-over portion has a length measured from the proximal waist of the occlusion balloon to the proximalmost extent of the occlusion balloon, wherein the length measured from the distal waist of the occlusion balloon to the distalmost extent of the occlusion balloon is greater than the length measured from the proximal waist of the occlusion balloon to the proximalmost extent of the occlusion balloon; wherein the sum of the lengths of the first folded-over portion and the second folded-over portion is greater than the length of the stent;
   wherein the occlusion balloon is configured to roll onto itself in the inflated state as the inflation balloon and stent are advanced across the lesion; and
   wherein the distalmost extent of the occlusion balloon is proximal of the stent in the pre-inflated state.

2. The stent delivery catheter of claim 1, wherein the elongate shaft includes a first inflation lumen in fluid communication with the inflation balloon and a second inflation lumen in fluid communication with the occlusion balloon.

3. The stent delivery catheter of claim 2, wherein the elongate shaft includes one or more inflation ports positioned between the proximal waist of the occlusion balloon and the distal waist of the occlusion balloon.

4. The stent delivery catheter of claim 3, wherein the one or more inflation ports fluidly connect the second inflation lumen with an interior of the occlusion balloon.

5. The stent delivery catheter of claim 1, wherein the elongate shaft includes a proximal tubular member and a distal tubular member extending distal of a distal end of the proximal tubular member, wherein a funnel-shaped fluid discharge port is located at the distal end of the proximal tubular member.

6. The stent delivery catheter of claim 5, wherein the funnel-shaped fluid discharge port surrounds the distal tubular member of the elongate shaft.

7. The stent delivery catheter of claim 1, wherein the occlusion balloon includes an occlusion balloon wall having an exterior surface and an interior surface;
   wherein the first folded-over portion of the occlusion balloon includes a first layer of the occlusion balloon wall and a second layer of the occlusion balloon wall located radially outward from the first layer of the occlusion balloon wall; and
   wherein the second folded-over portion of the occlusion balloon includes a first layer of the occlusion balloon wall and a second layer of the occlusion balloon wall located radially outward from the first layer of the occlusion balloon wall.

8. The stent delivery catheter of claim 7, wherein a portion of the first layer of the first folded-over portion of the occlusion balloon wall everts into a portion of the second layer of the first folded-over portion of the occlusion balloon wall as the occlusion balloon rolls onto itself.

9. The stent delivery catheter of claim 8, wherein a portion of the second layer of the second folded-over portion of the occlusion balloon wall everts into a portion of the first layer of the second folded-over portion of the occlusion balloon wall as the occlusion balloon rolls onto itself.

10. A stent delivery catheter for positioning a stent across a lesion of a blood vessel, the stent delivery catheter comprising:
an elongate shaft having a proximal end, a proximal region proximate the proximal end, a distal end, and a distal region proximate the distal end;
a stent having a proximal end, a distal end and a length from the proximal end to the distal end, the stent mounted on the distal region of the elongate shaft;
an occlusion balloon secured to the elongate shaft proximal of the proximal end of the stent, the occlusion balloon having a proximal waist secured to the elongate shaft and a distal waist secured to the elongate shaft, the occlusion balloon including a first folded-over portion extending distal of the distal waist to a distalmost extent of the occlusion balloon and a second folded-over portion extending proximal of the proximal waist to a proximalmost extent of the occlusion balloon, the occlusion balloon being inflatable from a pre-inflated state to an inflated state; and
a fluid discharge port concentrically disposed about the elongate shaft;
wherein when the occlusion balloon is in the pre-inflated state the first folded-over portion has a length measured from the distal waist of the occlusion balloon to the distalmost extent of the occlusion balloon and the second folded-over portion has a length measured from the proximal waist of the occlusion balloon to the proximalmost extent of the occlusion balloon, wherein the length measured from the distal waist of the occlusion balloon to the distalmost extent of the occlusion balloon is greater than the length measured from the proximal waist of the occlusion balloon to the proximalmost extent of the occlusion balloon; wherein the sum of the lengths of the first folded-over portion and the second folded-over portion is greater than the length of the stent;
wherein the distalmost extent of the occlusion balloon is proximal of the stent in the pre-inflated state; and
wherein the occlusion balloon is configured to roll onto itself in the inflated state as the stent is advanced across the lesion.

11. The stent delivery catheter of claim 10, wherein the fluid discharge port is configured to discharge a lubricious fluid toward the stent.

12. The stent delivery catheter of claim 10, wherein the fluid discharge port is located along the elongate shaft proximal of the stent.

13. The stent delivery catheter of claim 12, wherein the fluid discharge port is located distal of the occlusion balloon.

14. The stent delivery catheter of claim 10, wherein the elongate shaft includes a proximal tubular member and a distal tubular member extending distal of a distal end of the proximal tubular member, wherein the fluid discharge port is located at the distal end of the proximal tubular member.

15. The stent delivery catheter of claim 14, wherein the fluid discharge port is a funnel-shaped portion of the proximal tubular member of the elongate shaft.

16. The stent delivery catheter of claim 10, wherein the elongate shaft includes one or more inflation ports positioned between the proximal waist of the occlusion balloon and the distal waist of the occlusion balloon, the one or more inflation ports configured to fluidly connect an interior of the occlusion balloon to an inflation lumen extending through the elongate shaft.

17. The stent delivery catheter of claim 10, wherein the occlusion balloon includes an occlusion balloon wall having an exterior surface and an interior surface;
wherein the first folded-over portion of the occlusion balloon includes a first layer of the occlusion balloon wall and a second layer of the occlusion balloon wall located radially outward from the first layer of the occlusion balloon wall; and
wherein the second folded-over portion of the occlusion balloon includes a first layer of the occlusion balloon wall and a second layer of the occlusion balloon wall located radially outward from the first layer of the occlusion balloon wall.

18. The stent delivery catheter of claim 17, wherein a portion of the first layer of the first folded-over portion of the occlusion balloon wall everts into a portion of the second layer of the first folded-over portion of the occlusion balloon wall and a portion of the second layer of the second folded-over portion of the occlusion balloon wall everts into a portion of the first layer of the second folded-over portion of the occlusion balloon wall as the occlusion balloon rolls onto itself.

* * * * *